US011130679B2

(12) United States Patent
Moghaddam et al.

(10) Patent No.: US 11,130,679 B2
(45) Date of Patent: Sep. 28, 2021

(54) BIODEGRADABLE HOLLOW NANOPARTICLES AND METHODS AND APPARATUS FOR MANUFACTURING THE SAME

(71) Applicant: University of Utah Research Foundation, Salt Lake City, UT (US)

(72) Inventors: Seyyed Pouya Hadipour Moghaddam, Salt Lake City, UT (US); Hamidreza Ghandehari, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 45 days.

(21) Appl. No.: 16/294,872

(22) Filed: Mar. 6, 2019

(65) Prior Publication Data
US 2020/0071172 A1 Mar. 5, 2020

Related U.S. Application Data

(60) Provisional application No. 62/639,333, filed on Mar. 6, 2018.

(51) Int. Cl.
*A61K 9/51* (2006.01)
*B82Y 30/00* (2011.01)
(Continued)

(52) U.S. Cl.
CPC ............... *C01B 33/18* (2013.01); *B82Y 30/00* (2013.01); *B82Y 40/00* (2013.01);
(Continued)

(58) Field of Classification Search
None
See application file for complete search history.

(56) References Cited

U.S. PATENT DOCUMENTS 6,221,326 B1 * 4/2001 Amiche ............. B01J 20/28019
423/335
6,696,258 B1 * 2/2004 Wei ...................... A61K 9/143
423/702
(Continued)

FOREIGN PATENT DOCUMENTS

CN          102167336 A      8/2011
CN          102530969 A      7/2012
(Continued)

OTHER PUBLICATIONS

Wei Li et al, Investigation of selective etching mechanism and its dependency on the particle size in preparation of hollow silica spheres 2015, J Nanopart Res, 17:480, pp. 1-11. (Year: 2015).*

(Continued)

*Primary Examiner* — Stephanie P Duclair
(74) *Attorney, Agent, or Firm* — Terrence J. Edwards; TechLaw Ventures, PLLC

(57) ABSTRACT

The disclosure extends to biodegradable hollow nanoparticles, and systems, methods, devices, and processes for producing the same. The disclosure includes a method of preparing a hollow mesoporous nanoparticle by providing a plurality of silica core particles. Each of the plurality of silica core particles comprises a diameter within a range of about 600 nanometers to about 30 nanometers. The method further includes synthesizing a mesoporous silica shell around the plurality of silica core particles forming a plurality of mesoporous coated silica core particles. Further, the method provides for etching the plurality of mesoporous coated silica core particles with an aqueous solution of sodium carbonate and water to remove the silica core particle from the plurality of mesoporous coated silica core particles forming a plurality of hollow mesoporous particles. The method also includes diffusing a payload into the
(Continued)

plurality of hollow mesoporous particles in an aqueous solution.

21 Claims, 13 Drawing Sheets

(51) Int. Cl.
*B82Y 40/00* (2011.01)
*C01B 33/18* (2006.01)

(52) U.S. Cl.
CPC ...... *C01P 2004/34* (2013.01); *C01P 2004/64* (2013.01); *C01P 2006/16* (2013.01)

(56) References Cited

U.S. PATENT DOCUMENTS

| | | | |
|---|---|---|---|
| 9,271,936 B2 | 3/2016 | DeShong et al. | |
| 2014/0272573 A1 | 9/2014 | Xiao et al. | |
| 2014/0356623 A1* | 12/2014 | Yu | B01J 13/02 428/402 |
| 2017/0119688 A1* | 5/2017 | De Cola | A61K 9/5115 |

FOREIGN PATENT DOCUMENTS

| | | |
|---|---|---|
| CN | 105561345 A | 5/2016 |
| CN | 106000246 * | 10/2016 |
| CN | 108837161 A | 11/2018 |
| KR | 101399344 B1 | 5/2014 |
| WO | 2013123517 A1 | 8/2013 |
| WO | 2015/189402 * | 12/2015 |
| WO | 2016164987 A1 | 10/2016 |

OTHER PUBLICATIONS

Manuel Quesada et al, Hybrid PLGA-Organosilica Nanoparticles with Redox-Sensitive Molecular Gates 2013, Chemistry of Materials, 25, pp. 2597-2602. (Year: 2013).*
(ISA/US) "Notification of Transmittal of the International Search Report and the Written Opinion of the International Searching Authority, or the Declaration," PCT/US19/21054, dated Jun. 7, 2019.
Pouya et al., "Glutathione-sensitive hollow mesoporous silica nanoparticles for controlled drug delivery," Journal of Controlled Release, vol. 282 (Jul. 28, 2018); pp. 62-75; entire document.
Machine translation of Chinese Publication No. 105561345.
Machine translation of Chinese Publication No. 108837161.
Machine translation of Chinese Publication No. 102167336.
Machine translation of Chinese Publication No. 102530969.
Machine translation of Korean Publication No. 10-1399344.

* cited by examiner

US 11,130,679 B2

BIODEGRADABLE HOLLOW NANOPARTICLES AND METHODS AND APPARATUS FOR MANUFACTURING THE SAME

FEDERALLY SPONSORED RESEARCH OR DEVELOPMENT

This invention was made with government support under Grant Number R01 ES024681 awarded by the National Institutes of Health. The government has certain rights in the invention.

BACKGROUND

The disclosure relates to hollow silica nanoparticles and methods, systems, and devices for manufacturing the same. More particularly, the disclosure relates to a process, method, system, and apparatus for preparing biodegradable hollow nanoparticles for intracellular delivery of bioactive agents.

Silica nanoparticles ($SiO_2$ NPs) have drawn significant attention for delivery of bioactive agents due to their ease of synthesis, chemical robustness, and improved physiochemical control. Systems in the prior art are known to have issues with persistence, accumulation, and toxicity due to non-degradability.

The disclosure relates to biodegradable silica (Si—O—Si) nanoparticles ( . . . Si—O—Si . . . ) comprising hydrophilic properties. This is opposed to biodegradable hydrophobic silicone nanoparticles ( . . . Si—Si . . . ) which are known in the art and are less biocompatible and less suitable for use in aqueous environments. Biodegradable $SiO_2$ NPs may have application in agriculture as a method for delivering micronutrients, fertilizers, herbicides, fungicides, and pesticides. Biodegradable hollow mesoporous $SiO_2$ NPs may have higher loading capacity, lower toxicity, and greater environmental compatibility than applications known in the art.

BRIEF DESCRIPTION OF THE DRAWINGS

Non-limiting and non-exhaustive implementations of the disclosure are described with reference to the following figures, wherein like reference numerals refer to like parts throughout the various views unless otherwise specified. Advantages of the disclosure will become better understood with regard to the following description and accompanying drawings where.

DETAILED DESCRIPTION

Figure 1:
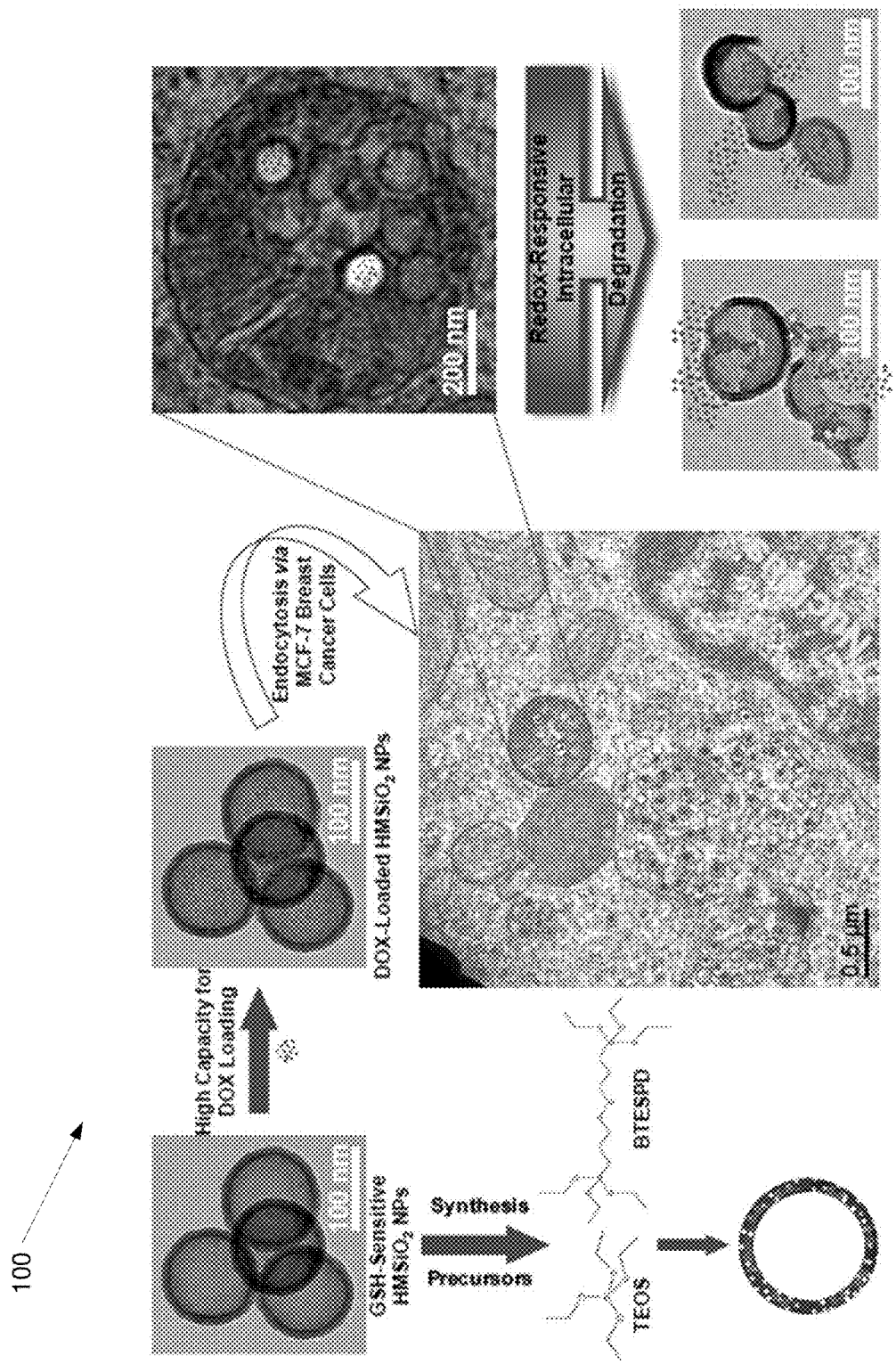
FIG. 1 illustrates a schematic overview diagram of a method for producing, loading, testing, and the degradation of a hollow nanoparticle using structural difference-based selective etching, according to one implementation.

The disclosure extends to hollow nanoparticles and methods, systems, devices, and processes for preparing the same.

Before the methods, systems, devices, and processes for preparing hollow nanoparticles are described, it is to be understood that this disclosure is not limited to the configurations, process steps, and materials disclosed herein as such configurations, process steps, and materials may vary somewhat. It is also to be understood that the terminology employed herein is used for describing implementations only and is not intended to be limiting since the scope of the disclosure will be limited only by the appended claims and equivalents thereof.

In describing and claiming the disclosure, the following terminology will be used in accordance with the definitions set out below.

It must be noted that, as used in this specification and the appended claims, the singular forms "a," "an," and "the" include plural referents unless the context clearly dictates otherwise.

As used herein, the terms "comprising," "including," "containing," "characterized by," and grammatical equivalents thereof are inclusive or open-ended terms that do not exclude additional, unrecited elements or method steps.

As used herein, the phrase "consisting of" and grammatical equivalents thereof exclude any element, step, or ingredient not specified in the claim.

As used herein, the phrase "consisting essentially of" and grammatical equivalents thereof limit the scope of a claim to the specified materials or steps and those that do not materially affect the basic and novel characteristic or characteristics of the claimed disclosure.

It will be appreciated that the biodegradable SiO2 NPs of the disclosure are applicable to many different uses, fields and applications. Biodegradable SiO2 NPs have application in plant science as products and methods for delivering macronutrients, secondary nutrients, micronutrients, non-essential beneficial elements, plant hormones, biostimulants, fertilizers, herbicides, fungicides, DNA, RNA, insecticides, biofertilizers, biopesticides, fruit ripening chemistries, ripening suppression chemistries, and fruit shelf-life enhancement chemistries. Biodegradable SiO2 NPs have application in animal science as products and methods for delivering carbohydrates, fats, minerals, proteins, dietary supplements, vitamins and other antioxidants, antibiotics, hormones, DNA, and RNA. Biodegradable SiO2 NPs have application in pest control as products and methods for delivering insect repellents, insecticides, DNA, and RNA. Biodegradable SiO2 NPs have application in medicine as products and methods or as a drug delivery system that may be incorporated with drugs, DNA, RNA, and medical imaging agents. Biodegradable SiO2 NPs also have application in nutraceuticals and human nutrition as products and methods for delivering carbohydrates, fats, minerals, proteins, bioactive plant extracts, dietary supplements, vitamins and other antioxidants, antibiotics, hormones, DNA, and RNA. Biodegradable SiO2 NPs have application in cosmetic applications as products and methods for skin treatments, skin care products, and other cosmetic applications.

Biodegradable $SiO_2$ NPs have potential to create a platform for safe and effective drug delivery, medical imaging agents, and agricultural applications. Regular mesoporous as well as non-porous silica nanoparticles (Si—O—Si) do not degrade over time which can cause toxicities in many applications. Biodegradable hollow Silica (Si—O—Si—S—S—Si—O—Si) nanoparticles are hydrophilic and not previously disclosed in the art. Biodegradable hydrophobic silicone nanoparticles (Si—Si) are known in the art and are less compatible in aqueous applications or biological applications.

Biodegradable $SiO_2$ NPs have application in agriculture as a method for delivering micronutrients, fertilizers, herbicides, fungicides, and pesticides. $SiO_2$ NPs can increase productivity in such applications by greater than 30%, which is a substantial increase in capacity. Biodegradable mesoporous and nonporous SiO2 NPs may be highly useful in medicine as a drug delivery system that may be incorporated with drugs and medical imaging agents. Such particles can be biodegraded inside the cells over time to significantly reduce the usual toxicity of non-biodegradable nanoparticles.

It should be appreciated that free ions, fertilizers, and pesticides are frequently sequestered, non-absorbed, or mitigated through resistance during biological application. The formation of nanoparticles can overcome such challenges by altering the way the particles interact with, for example, agricultural crops. Nanoparticle interactions include controlled release over extended periods, enhanced permeation through leaves and roots, the prevention of degradation by microbes, and various environmental factors. Because SiO2 NPs as disclosed are degradable in a tunable fashion, the regulatory considerations for environmental impacts may be minimized. Alternatively, non-degradable systems require years of environmental impact and toxicity analysis prior to use on agricultural crops.

Biodegradable mesoporous and non-porous SiO2 NPs may be useful in agriculture as a new delivery system that may be incorporated for fertilization and other applications. Such particles may be biodegraded inside the cells of crops over time to significantly reduce the usual toxicity of non-biodegradable nanoparticles. Hollow SiO2 NPs provide a unique structure that results in chemical stability, surface functionality, and biocompatibility. The utilization of SiO2 NPs can lead to good control on the release of loaded components in various applications, including agricultural applications.

In an embodiment, a method of synthesis is provided that is highly scalable and can be optimized for large scale production of hollow nanoparticles. Such synthesis may utilize bulk and commodity agents to increase the economic benefits of producing the nanoparticles. In an embodiment, the method includes synthesizing dense Stöber $SiO_2$ NPs via a modified Stöber method using a TEOS precursor. The method includes coating the Stöber particle with a surfactant-based mesoporous shell. The shell comprises Si—O—Si—C—C—C—S—S—C—C—C—Si—O—Si (in GSH-sensitive $HMSiO_2$ NPs) and Si—O—Si (in TEOS $HMSiO_2$ NPs) bonds. The bonds are coated on the surface of the Stöber cores using TEOS and bis[3-(triethoxysilyl)propyl] disulfide (BTESPD) precursors. The method includes forming a hollow structure using a high concentration of sodium carbonate ($Na_2CO_3$).

In an embodiment of the disclosure, a method for preparing a hollow mesoporous nanoparticle is described. The method includes providing a plurality of core nanoparticles and coating each of the plurality of core nanoparticles with tetraethyl orthosilicate (TEOS) and bis[3-(triethoxysilyl)propyl] disulfide (BTESPD) to provide a surfactant-based mesoporous shell around each of the plurality of core nanoparticles. The method further includes etching a majority of each of the plurality of core nanoparticles using an etchant to create a plurality of hollow mesoporous nanoparticle structures each having a surfactant-based mesoporous shell. The method is such that the surfactant-based mesoporous shell comprises a range of about 1% TEOS to 99% BTESPD. In an alternative embodiment, the range of about 80% TEOS to about 20% BTESPD.

In an embodiment of the disclosure, a glutathione (GSH)-sensitive hollow mesoporous SiO2 NP is developed using structural difference-based selective etching. The organosilica nanoreservoirs include disulfide linkages (S—S) in an outer shell that may be degraded via intracellular GSH. In an embodiment, transmission electron microscopy (TEM) indicates that fabricated SiO2 NPs comprise an average diameter of 130±5 nm. Thermogravimetric analysis (TGA) indicates that GSH-sensitive particles comprise approximately 5.3% more weight loss than TEOS hollow SiO2 NPs; this may be attributed to the disulfide containing organosilicon matter. Zeta potential of the redox-responsive particles is about −23±1 mV at pH 6 in deionized (DI) water. Nitrogen adsorption-desorption isotherm indicates that the surface area of the hollow mesoporous nanoreservoirs is about 446±6 $m^2$/g and the average diameter of the pores is about 2.3±0.5 nm. Hollow silica nanobubbles demonstrate high loading capacity for DOX that is directly proportional to the voids existing in the hollow structures. In an embodiment, approximately 58% of the incorporated DOX released within fourteen days in phosphate buffered saline (PBS) at pH 6 and 10 mM GSH mimicking intracellular tumor microenvironment while release from TEOS hollow $SiO_2$ NPs was 18%.

In an embodiment of the disclosure, there is described GSH-sensitive biodegradable hollow mesoporous silica nanoparticles ($HMSiO_2$ NPs) comprising disulfide bonds. Such nanoreservoirs are fabricated based on controlled reaction conditions and structural difference-based selective etching techniques in which a core-shell structure is created with distinct structural and compositional differences between the inner dense silica core and the outer disulfide-based mesoporous silica shell. In an embodiment, the inner core is selectively etched away by applying an appropriate etching agent, while the outer shell remains mostly intact and ultimately a hollow nanoparticle is formed. A redox-triggered degradable system as disclosed can combine the advantages of degradability, high loading efficiency, sustained drug or plant nutrient release via tunable interior hollow cavity diameter, pore size, shell thickness, ease of fabrication, stability, and ability to scale up.

It should be appreciated that an embodiment of the disclosure may be utilized in various fields, including for example, human nutrition, nutraceutical, agriculture, oil and gas, and industrial applications. Example human nutrition or nutraceutical applications include providing a nutrient to a user, for example a microbiome in a controlled release. Example industrial applications include providing the hollow nanoparticles for de-icing applications, for example for the application of a de-icing particle for airplanes or roadways. Further example applications include agricultural applications, including providing fertilizer, fungicide, pesticide, and so forth. Further example applications include providing a medication to a patient, for example an anti-cancer medication that may specifically attack cancer cells in a controlled release fashion.

Referring now to FIG. 1, there is illustrated a schematic overview diagram of a method 100 for producing, loading, testing, and the degradation of a hollow nanoparticle using structural difference-based selective etching.

Figure 2:
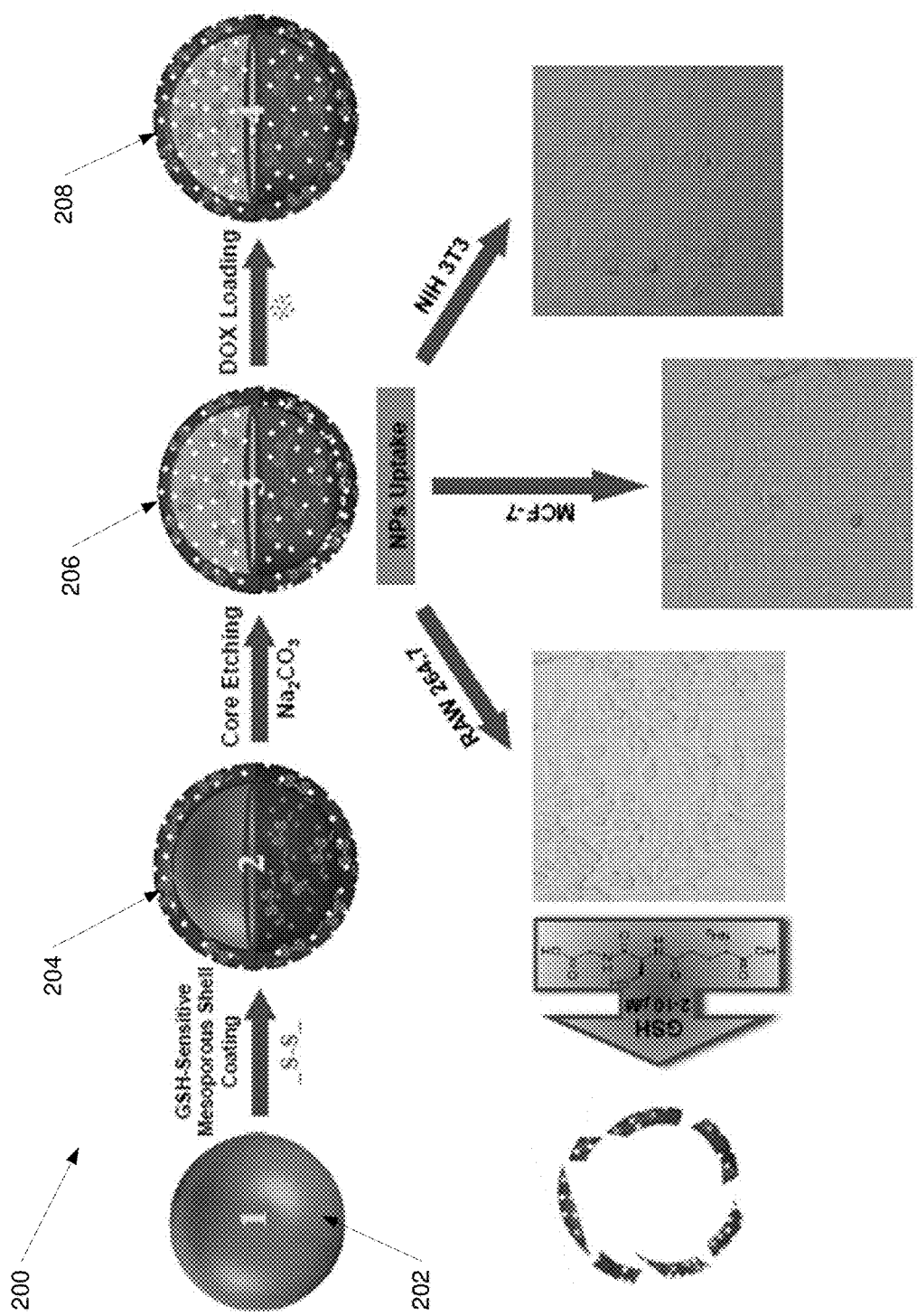
FIG. 2 illustrates a schematic overview diagram of a method for the production, loading, and degradation of a hollow nanoparticle, according to one implementation.

FIG. 2 illustrates a schematic overview diagram of a method 200 for producing a hollow nanoparticle. $HMSiO_2$ NPs are fabricated using unique structural/compositional difference-based (between the core and the shell) selective etching strategies.

The method 200 includes at least three steps for the preparation of the hollow nanostructures. Step one 202 includes synthesizing dense Stöber NPs via a modified Stöber method using TEOS precursor. The Stöber cores are considered a hard template.

Step two 204 includes a surfactant-based mesoporous shell comprising Si—O—Si—C—C—C—S—S—C—C—C—Si—O—Si (in GSH-sensitive $HMSiO_2$ NPs) and Si—O—Si (in TEOS $HMSiO_2$ NPs) bonds. The bonds are coated on the surface of the Stöber cores using TEOS and bis[3-(triethoxysilyl)propyl] disulfide (BTESPD) precursors. The hollow cavity and the shell thickness may be controllable by altering the size of the hard template and the amount of the precursor used in the process of core-shell formation, respectively.

Figure 3:
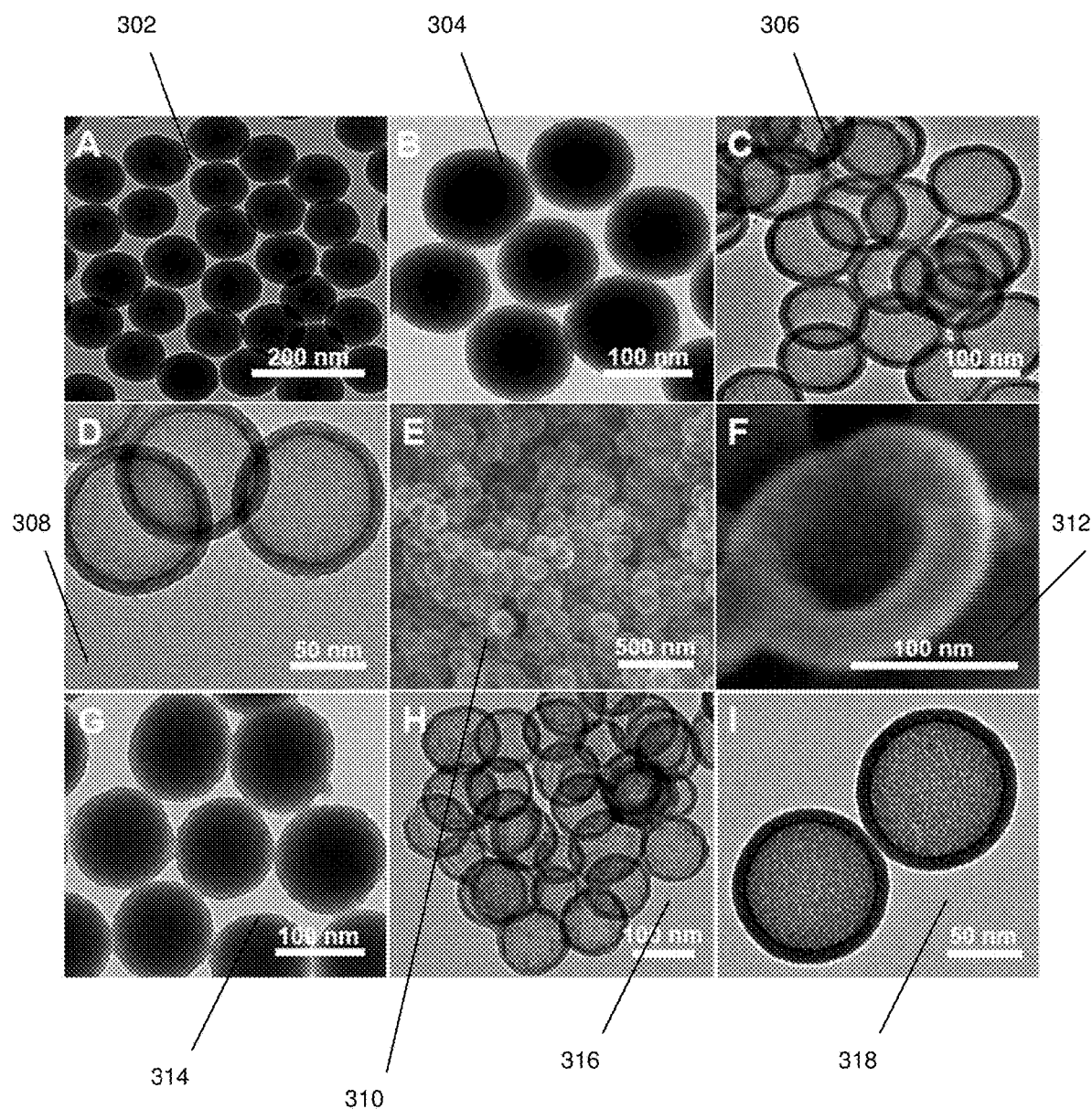
FIG. 3 illustrates electron microscopy images of various particles, according to one implementation.

Step three 206 includes forming a hollow structure using a high concentration of sodium carbonate ($Na_2CO_3$).The hollow particles can be reduced via intracellular GSH FIG. 3 illustrates electron microscopy images of various particles. Reference 302 illustrates a uniform 100 nm core Stöber nanoparticle. Reference 304 illustrates a disulfide-based mesoporous shell coated Stöber nanoparticle synthesized by the addition of TEOS and BTESPD precursors. References 306 and 308 illustrate a GSH-sensitive $HMSiO_2$ nanoparticle under two magnifications. Reference 310 illustrates a scanning electron microscope image of a GSH-sensitive $HMSiO_2$ nanoparticle. Reference 312 illustrates a broken nanoparticle having a voluminous hollow interior. Reference 314 illustrates a mesoporous shell coated Stöber nanoparticle synthesized by the addition of TEOS. References 316 and 318 illustrate TEOS $HMSiO_2$ nanoparticles under two magnifications.

As illustrated in FIG. 3, uniform Stöber particles are synthesized with an average diameter of approximately 100±5 nm and coated with 15 nm mesoporous shell using hydrolysis and co-condensation of silane precursors. The porosity of the shell is evident in the images (see 306 and 308). Uniform GSH-sensitive $HMSiO_2$ NPs with an average diameter of approximately 130±5 nm were obtained by selective etching strategy due to the structural and compositional differences between the inner core and the outer shell in the core-shell particles while TEOS $HMSiO_2$ NPs were achieved via structural difference between the core and the shell (see 316 and 318). It will be appreciated that the disclosure may utilize a plurality of silica core particles (Stöber particles), wherein each of the plurality of silica core particles comprise a diameter that may be within a range of about 600 nanometers to about 30 nanometers.

To achieve the hollow nanostructures as shown in FIG. 3, several etching strategies were applied. A first strategy includes etching via hydrochloric acid and sodium chloride solution in which high temperature (approximately 150 Centigrade) was applied to the core-shell particles but almost no etching was observed. This method may be described as hydrothermal treatment. A second strategy includes providing hydrofluoric acid (HF) as an etchant. A high concentration of HF was provided, such as 10% in water for 10 minutes at 50 Centigrade. A third strategy includes utilizing sodium carbonate as an etchant for the nanoparticles. The reaction parameters for each of the aforementioned strategies may be optimized by changing, for example, the precursor ratio, the concentrations of nanoparticles, the rate of stirring, and the temperature.

Figure 7:
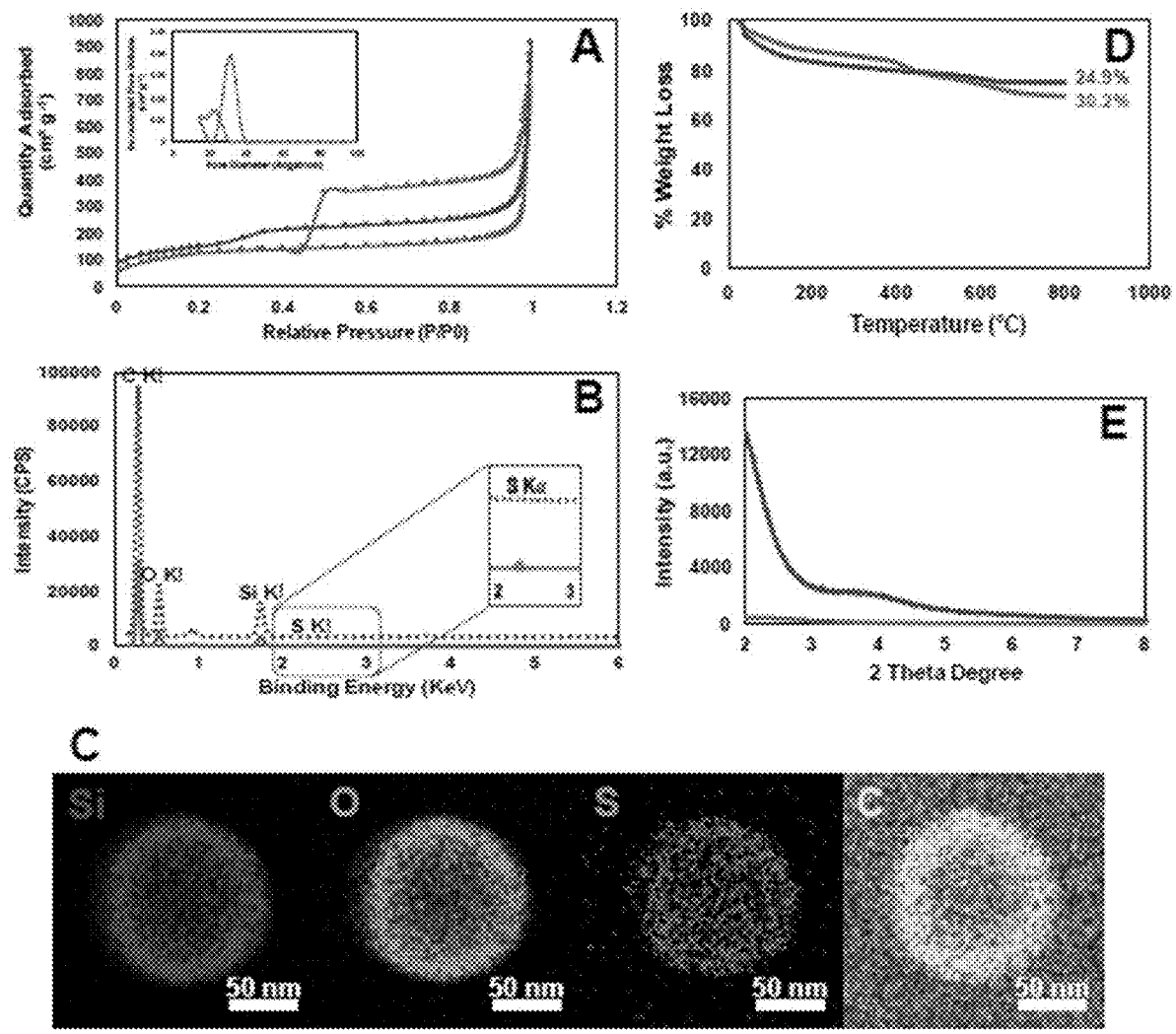
FIG. 7 illustrates graphs depicting nitrogen adsorption desorption isotherms, chemical composition, degradation, and pore characterization of nanoparticles, according to one implementation.

Further as illustrated in FIG. 3, 304 compares the structure and density difference between the silica Stöber core and the TEOS-BTESPD coating. As shown in FIG. 7 diagram B STEM spectra, sulfur peak can be observed in the binding energy around 2.3 KeV for GSH-sensitive particles. FIG. 7 image C indicates approximate atomic densities in GSH-sensitive $HMSiO_2$ NP via energy dispersive X-ray spectrometer (EDS) detector. This detector scans the surface of one NP in a raster pattern and confirms homogenous distribution of sulfur in the NP's outer shell. TGA in FIG. 7 diagram D demonstrates that GSH-sensitive $HMSiO_2$ NPs had weight loss of c.a. 30.2% while it was approximately 24.9% in TEOS $HMSiO_2$ NPs. This 5.3% difference in weight loss is attributed to the presence of organosilane portion ( . . . Si—C—C—C—S—S—C—C—C—Si . . . ) in disulfide-based particles and calcination of these groups. Loss of moisture exists within the NPs leads to weight loss less than 100° C.

XRD plot shown in FIG. 7 diagram E reveals that the mesopores existed in the shell of GSH-sensitive $HMSiO_2$ NPs (green line) had disordered structure since no typical Bragg peaks were observed at low 2θ areas. In XRD graph of TEOS $HMSiO_2$ NPs (310; red line), two broad peaks can be seen around 2 and 4 degrees which suggest short-range ordering and a wormlike pore structure in these NPs.

In an embodiment as indicated in FIG. 3, size, size distribution, and shape of fabricated $HMSiO_2$ NPs are characterized using transmission electron microcopy (TEM) and scanning electron microscopy (SEM). As shown (310), uniform Stöber particles were synthesized with an average diameter of c.a. 100±5 nm and coated with 15 nm mesoporous shell (304 and 314 for GSH-sensitive and TEOS $HMSiO_2$ NPs, respectively) using hydrolysis and co-condensation of silane precursors. The porosity of the shell is evident is these images. Reference numbers 306 and 308 indicate that uniform GSH-sensitive $HMSiO_2$ NPs with an average diameter of c.a. 130±5 nm were obtained by selective etching strategy due to the structural and compositional differences between the inner core and the outer shell exist in the core-shell particles while TEOS $HMSiO_2$ NPs were achieved via structural difference between the core and the shell (316, 318). Studies have also shown that cationic surfactants can protect the outer shell during the procedure. It is postulated that CTAB plays a key role in the generation of $HMSiO_2$ NPs from dense Stöber core by acting as a stabilizer to protect the silicate-CTAB shell from alkaline etching. Reference numbers 310 and 312 in FIG. 3 display SEM images of GSH-sensitive $HMSiO_2$ NPs and one broken particle which confirms the existence of spacious void in the hollow cavity, respectively. For obtaining these hollow nanostructures, several etching strategies were applied as follow: etching via hydrochloric acid (HCl)/sodium chloride (NaCl) solution in which high temperature (150° C.) was applied to the core-shell particles but almost no etching was observed. In another experiment, hydrofluoric acid (HF) was used as the etchant in which the etching time and HF concentration were played major roles for the etching process. With high concentration of HF (10% in water for 10 min at 50° C.) all the particles end up being broken. However, with lower concentration of HF (2.5%) and longer etching times (4 and 10 h at 50° C.), rattle-type particles were formed instead of hollow NPs. Finally, we realized that sodium carbonate is the best etchant for our NPs. In each experiment, different parameters where tested such as concentration of sodium carbonate, etching time, temperature, and stirring rate. However, it was understood that for effective etching of our $HMSiO_2$ NPs, the optimal condition is to use high concentration of Na2CO3 at 50° C. under vigorous stirring for 10 h. After optimizing reaction parameters, several GSH-sensitive $HMSiO_2$ NPs were fabricated with differences in size of the interior cavity and shell thickness. As previously noted, the disclosure may utilize silica core particles (Stöber particles) that comprise a diameter within a range of about 600 nanometers to about 30 nanometers.

Figure 4:
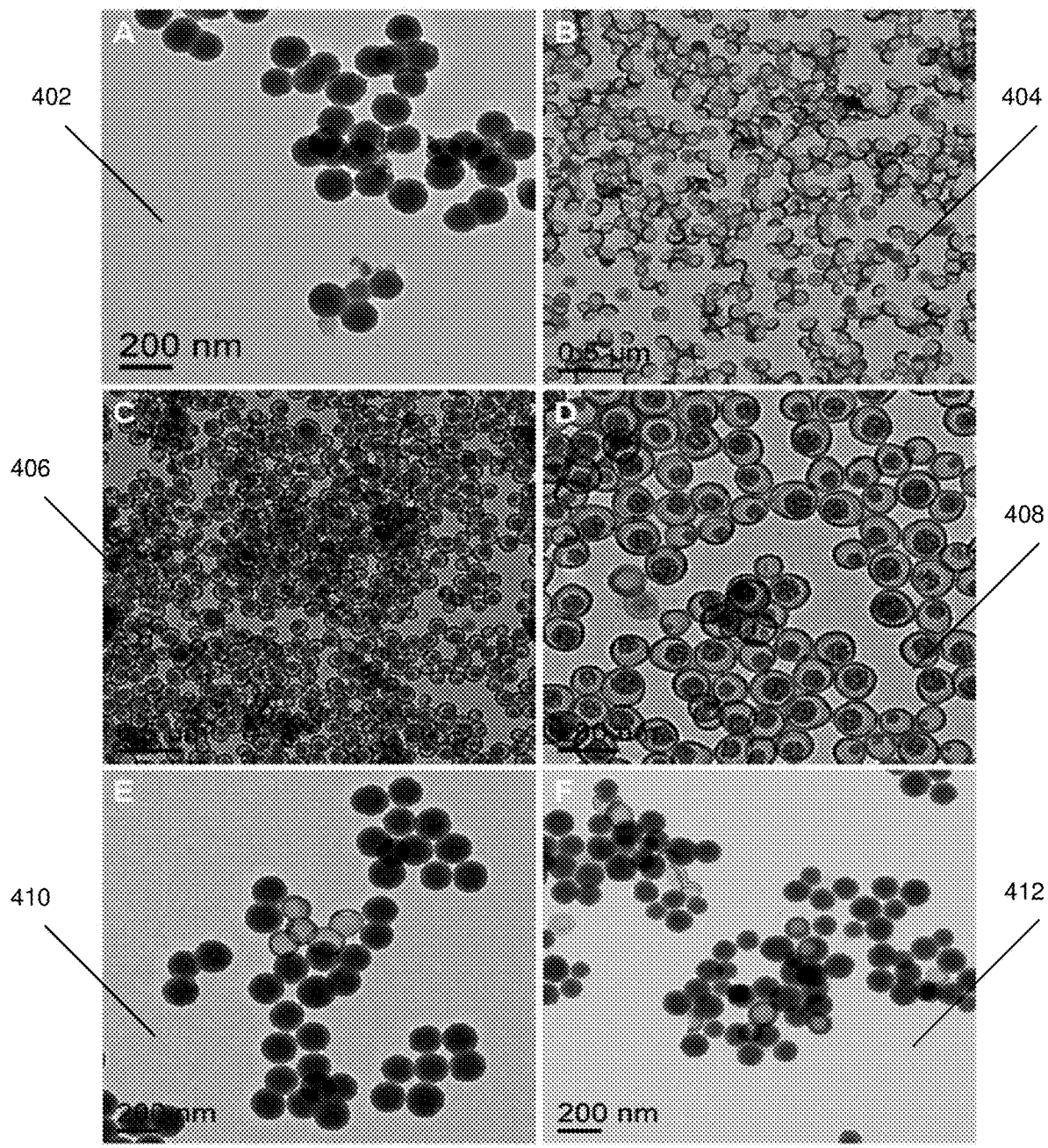
FIG. 4 illustrates electron microscopy images of various particles, according to one implementation.

FIG. 4 illustrates electron microscopy images of various particles. Image 402 illustrates etched particles using hydrochloric acid and sodium chloride solution at high temperature under constant stirring. Image 404 illustrates etched particles using 10% of hydrofluoric acid for 4 hours at 50° C. under constant stirring. Image 406 illustrates rattle-type particles formed by 2.5% of hydrofluoric acid for 10 hours at 50° C. under constant stirring. Image 408 illustrates rattle-type particles formed by 2.5% of hydrofluoric acid for 10 hours at 50° C. and under constant stirring. Image 410 illustrates etched particles using sodium carbonate (15 mmol) for 10 hours at 50° C. and under constant stirring. Image 412 illustrates etched particles using sodium carbonate (15 mmol) for 10 hours at 50° C. and under constant stirring with different TEOS/BTESPD ratio.

Figure 5:
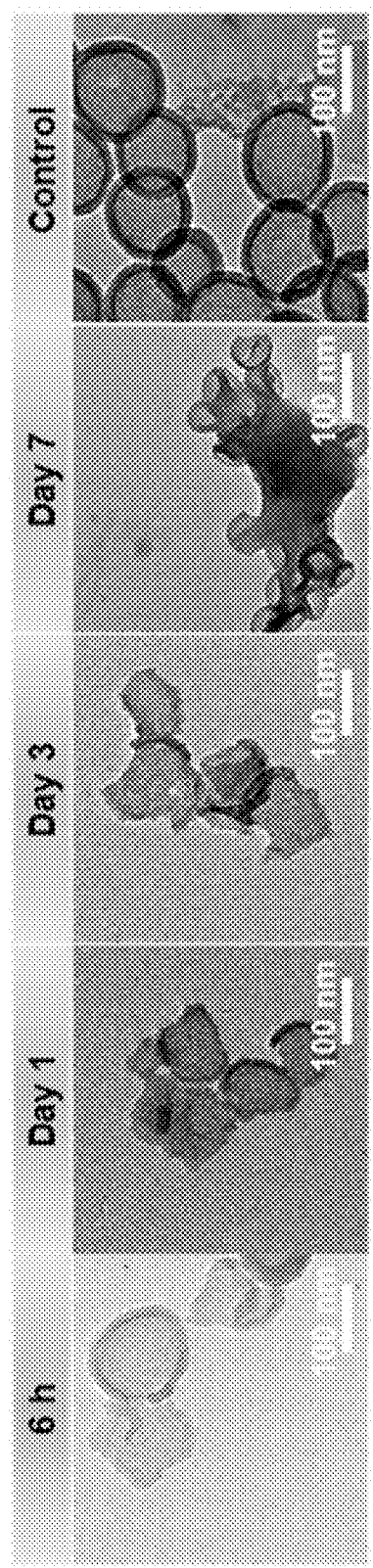
FIG. 5 illustrates a degradation of a nanoparticle over a period of time, according to one implementation.

FIG. 5 illustrates electron microscopy images for the degradation of GSH-sensitive $HMSiO_2$ nanoparticles in the presence of 10 mM of GSH in deionized water over a period of seven days.

Figure 6:
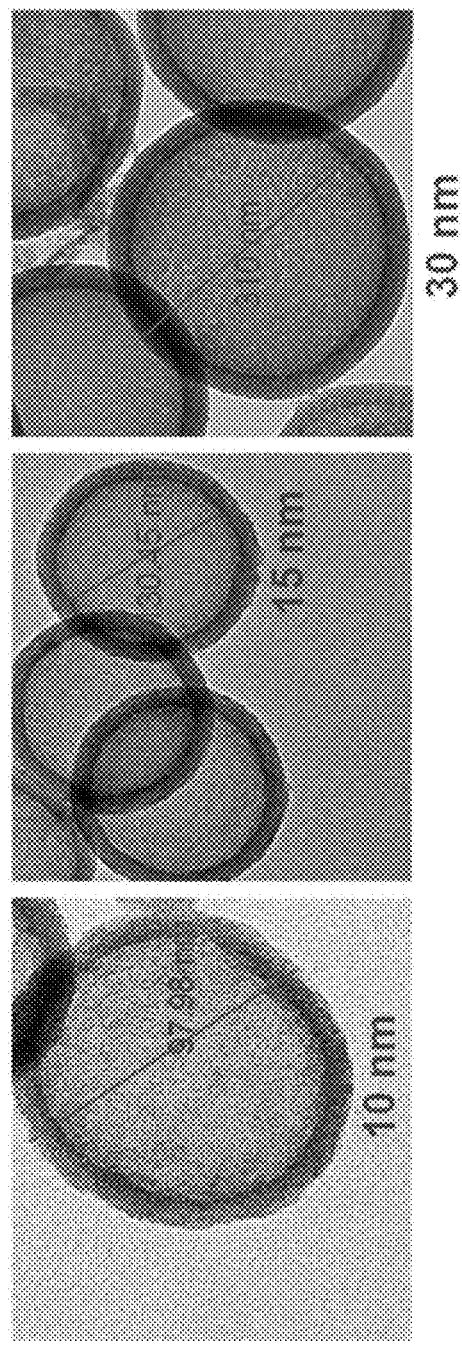
FIG. 6 illustrates electron microscopy images of various particles, according to one implementation.

FIG. 6 illustrates electron microscopy images of GSH sensitive $HMSiO_2$ nanoparticles showing tunable interior hollow cavities. The nanoparticles may have hollow cavities ranging from 80 to 250 nm and a mesoporous shell thickness ranging from about 10 to 30 nm depending on reaction parameters.

FIG. 7 images A-E illustrate further characterization of GSH-sensitive and TEOS $HMSiO_2$ NPs in terms of nitrogen adsorption desorption isotherms, thermogravimetric analysis (TGA), scanning transmission electron microscopy (STEM), and X-ray diffraction (XRD).

As illustrated in FIG. 7 in plot A, where the dotted lines represent TEOS $HMSiO_2$ NPs and the solid lines represent GSH-sensitive NPs, each exhibited sorption isotherms type IV which is ascribed to "mesoporous" NPs with average pore diameters of approximately 2.3 and 3.1 nm.

FIG. 7 illustrates nitrogen adsorption desorption isotherms of fabricated $HMSiO_2$ nanoparticles with and without hysteresis loop. FIG. 7 provides further characterization of GSH-sensitive and TEOS $HMSiO_2$ NPs in terms of nitrogen adsorption desorption isotherms, thermogravimetric analysis (TGA), scanning transmission electron microscopy (STEM), and X-ray diffraction (XRD). As indicated in FIG. 7, diagram A, GSH-sensitive and TEOS $HMSiO_2$ NPs exhibited sorption isotherms type IV which is ascribed to "mesoporous" NPs with average pore diameters of 2.3 nm and 3.1 nm.

As indicated in FIG. 7, diagram B, a comparison of sulfur density between GSH-sensitive and TEOS $HMSiO_2$ NPs is disclosed. As shown in STEM spectra, sulfur peak can be observed in the binding energy around 2.3 KeV for GSH-sensitive particles. Diagram C indicates approximate atomic densities in GSH-sensitive $HMSiO_2$ NP via energy dispersive X-ray spectrometer (EDS) detector.

In FIG. 7, diagram D, a GSH-sensitive $HMSiO_2$ NPs exhibit a weight loss of approximately 30.2% while it was approximately 24.9% in TEOS $HMSiO_2$ NPs. The 5.3% difference in weight loss is attributed to the presence of organosilane portion (Si—C—C—C—S—S—C—C—C—Si) in disulfide-based particles and calcination of such groups. FIG. 7, diagram E, illustrates that the mesopores existed in the shell of GSH-sensitive $HMSiO_2$ NPs.

Figure 8:
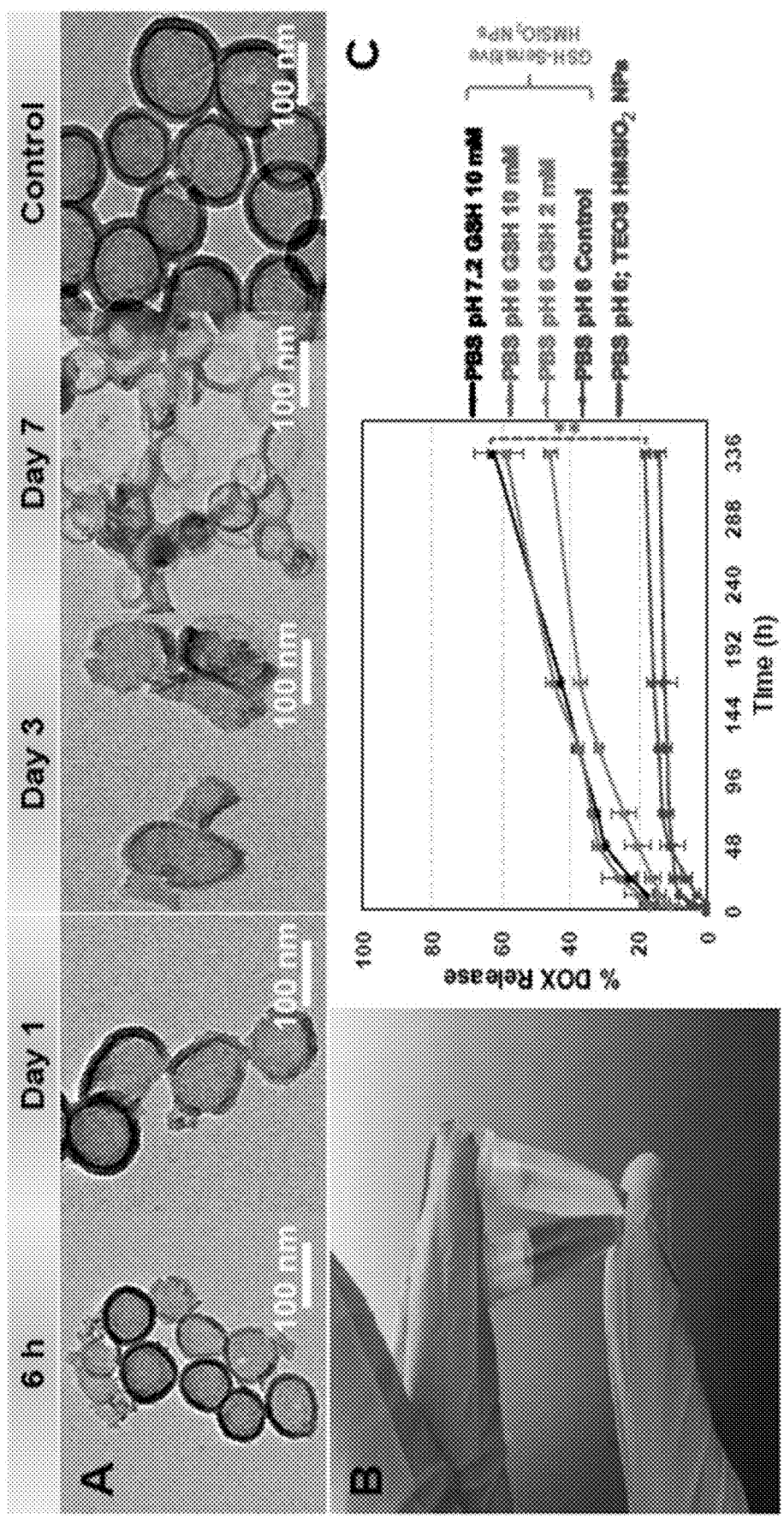
FIG. 8 illustrates electron microscopy images for the degradation of nanoparticles over a period of 14 days, the high loading capacity of the particles, and the release rate of the nanoparticles according to one implementation.

FIG. 8 illustrates electron microscopy images for the degradation of GSH-sensitive $HMSiO_2$ nanoparticles in the presence of 10 mM of GSH in deionized water for seven days. The control comprises NPs dispersed in DI water at 37° C. and pH 6 after day 7 (without GSH). Image B illustrates DOX solution before (left) and after (right) interaction with $HMSiO_2$ NPs. The image was captured after mixing, washing, and precipitating the NPs via centrifugation. High loading capacity 8.9±0.5% was observed with GSH-sensitive $HMSiO_2$ NPs. Graph C illustrates a DOX release profile from the GSH-sensitive and TEOS $HMSiO_2$ NPs in solutions of different pH at 37° C. for 14 days.

As further illustrated in FIG. 8, FIG. 8 diagram A illustrates in vitro degradation of GSH-sensitive $HMSiO_2$ NPs (50 µg $mL^{-1}$) in the presence of 10 mM of GSH at 37° C. and pH 6 for 7 days. This concentration was chosen to mimic intracellular concentration of GSH and pH 6 resembles pH of intracellular tumor microenvironment. GSH is a peptide composed of L-cysteine, glycine, and L-glutamic acid in which the L-cysteine amino acid have free S—H (thiol) group. These thiol groups can be oxidized to GSSG molecules and form an equilibrium. GSH is a leading intracellular compound for breaking of bioreducible carriers. It has been proposed that high intracellular concentrations of GSH (2-10 mM) can facilitate degradation of specific bonds. Moreover, extracellular concentrations of GSH are 100-1000 times lower (1-20 µM) than intracellular. To that end, these carriers can be applied in delivery systems when we need to have extracellular stability and release the payload only when the carriers are internalized. One of these linkages for achieving this goal is the disulfide bridges in the NPs' structure, for which intracellular GSH concentrations can be utilized for triggering thiol-disulfide exchange. It was observed that these redox-responsive hollow particles can start falling apart from the first hours (FIG. 8 diagram A). As shown, many of the particles degraded after day 7. Two mechanisms were observed for the degradation profile of these particles based on TEM images: first, majority of the NPs were broken down into smaller fragments. Second, some of the particles collapsed after day 7 which could result from loose structure of the shell when disulfide bonds started to break. In contrast, the particles in the control group after day 7, remained almost intact. It should be considered that the concentration of GSH is constant in vivo due to dynamic conditions and there is always an equilibrium between reduced glutathione (GSH) and oxidized (GSSG) one via glutathione peroxidase/reductase enzymes. Hence, it seems that we may have higher in vivo degradation of these GSH-sensitive $HMSiO_2$ NPs. Degradation of these particles at pH 7.2 and 10 mM of GSH was also performed. Results indicate that change in pH did not alter degradation of GSH-sensitive $HMSiO_2$ NPs. In addition, degradation was evaluated in the presence of 10 μM of GSH at pH 7.2.

$HMSiO_2$ NPs have been used as the delivery carriers due to their hollowness, low density, large surface area, and high drug loading capacity. For exploring drug loading capacity of GSH-sensitive and TEOS $HMSiO_2$ NPs, DOX, a water-soluble drug, was used as an anticancer drug model. DOX was physically incorporated in $HMSiO_2$ NPs. In this process, electrostatic interactions facilitate incorporation of positively charge DOX in negatively charged NPs. After physical mixing for 24 h and washing the product thoroughly, loading capacity for GSH-sensitive and TEOS $HMSiO_2$ NPs was 8.9±0.5% (which means approximately 89 μg of DOX exists per 1 mg of GSH-sensitive $HMSiO_2$ NPs) and 8.2±0.4%, respectively. This high loading capacity is directly related to interior cavity in these NPs and is proportional to the particle diameter which would be advantageous when there is a need to deliver two types of active agents simultaneously in the same carrier (co-delivery). FIG. 8 diagram B displays the GSH-sensitive hollow particles before and after interaction with DOX solution (100 μg $mL^{-1}$). Next, DOX release profile from GSH-sensitive and TEOS $HMSiO_2$ NPs in different pH values were evaluated for 14 days. Results (FIG. 8 diagram C) indicate redox-responsive hollow particles can release DOX approximately up to 60% in the presence of 10 mM of GSH in both pH 6 and pH 7.2. This release decreased when 2 mM of GSH was used at pH 6 and c.a. 45% of DOX released from the particles after 2 weeks. It was realized that release from control samples (GSH-sensitive $HMSiO_2$ NPs dispersed in PBS at pH 6 and without GSH) and TEOS $HMSiO_2$ NPs was approximately up to 14% and 18% (the difference is statistically significant in comparison to release in the presence of 10 mM of GSH), respectively. This suggests that DOX can be entrapped inside these hollow particles and release very slowly. In most samples, for the first 24 h, burst release was observed from the particles which results from the dissolution of DOX bound to the surface of the particles or entrapped in the pores of the shell.

Figure 9:
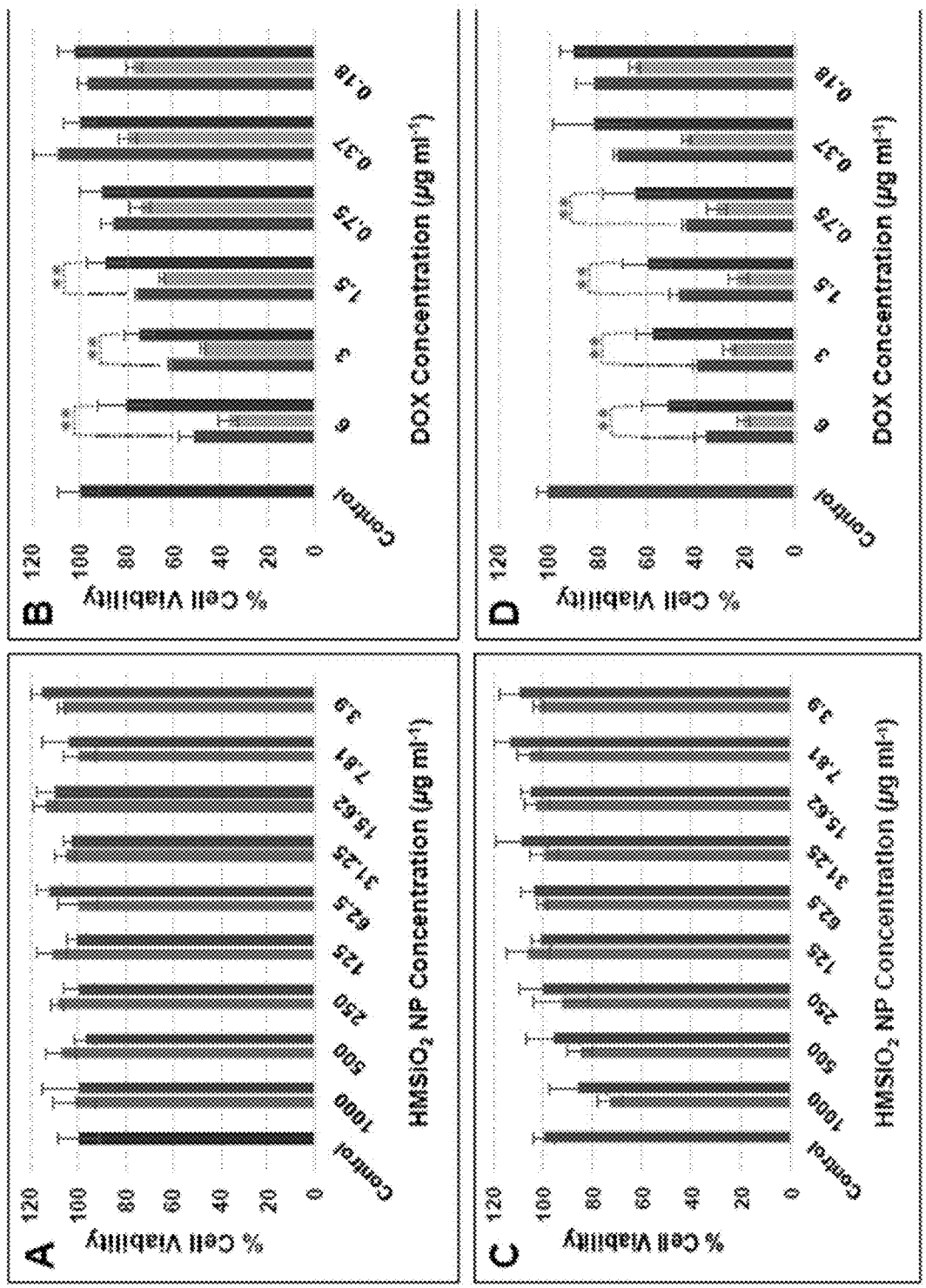
FIG. 9 illustrates graphs depicting cell toxicity of nanoparticles, according to one implementation.

FIG. 9 illustrates MCF-7 cell toxicity of GSH-sensitive $HMSiO_2$ nanoparticles and TEOS $HMSiO_2$ nanoparticles after incubation for (FIG. 9 diagram A) twenty-four hours and (FIG. 9 diagram C) forty-eight hours. FIG. 9 further illustrates MCF-7 cytotoxicity of DOX-loaded GSH-sensitive $HMSiO_2$ NPs, DOX-loaded TEOS $HMSiO_2$ NPs, and free DOX after incubation for 24 hours and 48 hours.

Further as illustrated in FIG. 9, cell toxicity of GSH-sensitive and TEOS $HMSiO_2$ NPs, DOX-loaded GSH-sensitive and TEOS $HMSiO_2$ NPs, and free DOX was evaluated in MCF-7 breast cancer epithelial cells after incubation for 24 and 48 h. Results (FIG. 9 diagram A) reveal that both GSH-sensitive and TEOS $HMSiO_2$ NPs were almost non-toxic to MCF-7 cells after incubation for 24 h in the concentration range between 3.9 to 1000 μg $mL^{-1}$. However, cell toxicity decreased when the cells were treated with concentration of NPs higher than 125 μg $mL^{-1}$ and incubated for 48 h (FIG. 9 diagram C). For GSH-sensitive $HMSiO_2$ NPs, this toxic effect started from 250 μg $mL^{-1}$ while for TEOS $HMSiO_2$ NPs toxicity was observed with the concentrations equal or greater than 500 μg $mL^{-1}$ which possibly results from the accumulation of particles inside these cells and disrupting cell membrane integrity.

To demonstrate that DOX-loaded hollow particles can have toxic effects on MCF-7 cells, cytotoxicity of these loaded particles were tested and compared with toxicity of free DOX. As shown in FIG. 9, diagrams B and D, cells were treated with DOX-loaded particles based on DOX concentration ranging from 0.18 to 6 μg $mL^{-1}$. It was understood that free DOX had higher toxic effects on MCF-7 cells than DOX-loaded particles with the maximum cell viability reduction of approximately 64% and 80% using 6 μg $mL^{-1}$ of DOX after incubation for 24 and 48 h, respectively. However, we should consider that free DOX molecules can kill normal cells too. So, just having higher cell viability reduction does not guarantee that free DOX has superiority compared to DOX-loaded GSH-sensitive $HMSiO_2$ NPs. However, between two fabricated hollow NPs, statistically significant difference was observed for the concentrations higher than 1.5 and 0.75 μg $mL^{-1}$ of DOX after incubation for 24 and 48 h, respectively. DOX-loaded GSH-sensitive $HMSiO_2$ NPs (containing 6 μg $mL^{-1}$ of DOX) killed c.a. 50% of the cells while DOX-loaded TEOS $HMSiO_2$ NPs with the same concentration killed 20% after 24 h incubation. This finding results probably from higher DOX release inside the cells due to disulfide-based particle degradation. Cell viability reduction reached to 64% and 49% after incubation for 48 h with DOX-loaded GSH-sensitive $HMSiO_2$ NPs and DOX-loaded TEOS $HMSiO_2$ NPs, respectively (containing 6 μg $mL^{-1}$ of DOX). This data suggests that there is an optimum concentration in which the intact hollow particles do not have toxic effects on the cells, but DOX-loaded particles can effectively kill c.a. 50% of the cancer cells. In these experiments, the optimum concentration of GSH-sensitive $HMSiO_2$ NPs is c.a. 66 μg $mL^{-1}$ which can hold 6 μg $mL^{-1}$ of DOX.

Figure 10:
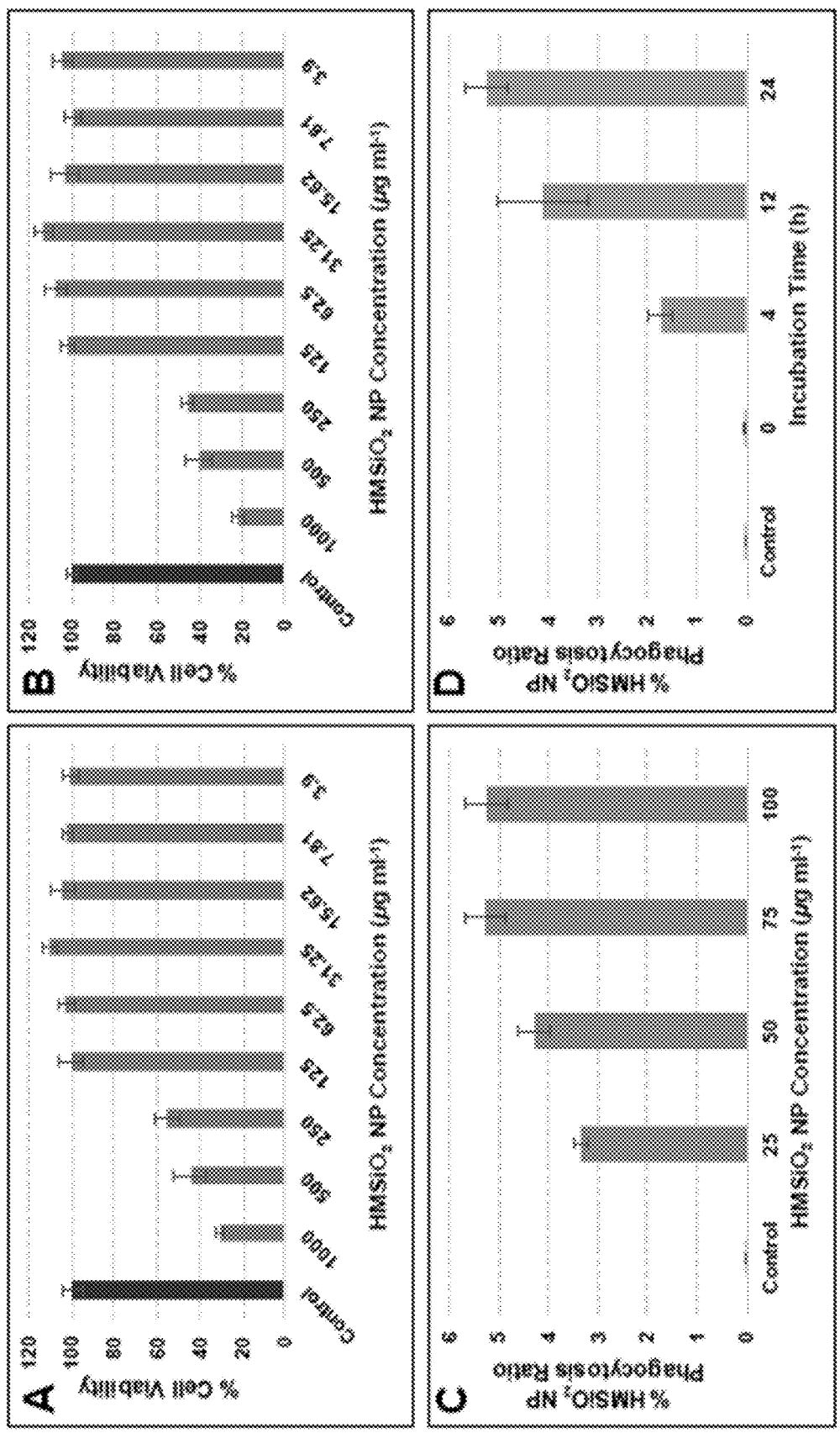
FIG. 10 illustrates graphs depicting cytotoxicity of nanoparticles, according to one implementation.

FIG. 10 illustrates cytotoxicity of GSH-sensitive $HMSiO_2$ nanoparticles in RAW 264.7 macrophages after incubation for (FIG. 10 diagram A) 24 hours and (FIG. 10 diagram B) 48 hours. In an embodiment, particles are toxic to the cells with the concentrations equal or greater than 250 μg $mL^{-1}$.

The primary role of macrophages is early uptake of foreign material and their clearance. They can easily ingest large materials such as cellular debris or bacteria. In this study, RAW 264.7 macrophage cell line was chosen due to their high phagocytic activity. As shown in FIGS. 12A and 12B, cell toxicity of GSH-sensitive $HMSiO_2$ NPs was evaluated in RAW 264.7 macrophages after incubation for 24 and 48 h, respectively. Results (FIG. 10 diagram A) indicate that unlike MCF-7 cells, these hollow particles had toxic effects on RAW 264.7 macrophages when the NP concentration was equal or greater than 250 μg $mL^{-1}$ and cell viability decreased c.a. 70% when the cells were co-cultured with 1000 μg $mL^{-1}$ of particles and incubated for 24 h. This toxicity was also time-dependent in which cell viability decreased c.a. 9% more under the same NP concentration and incubation for 48 h (FIG. 10 diagram B). Next, uptake of GSH-sensitive $HMSiO_2$ NPs (25-100 μg $mL^{-1}$ which is the maximum safe concentration of these hollow particles in RAW 264.7 macrophages after incubation for 24 h; FIG. 10 diagram C) was studied in RAW 264.7 macrophages which is also known as phagocytosis ratio. It was understood that after the dose of equal or greater than 75 μg $mL^{-1}$, a plateau was observed with the maximum uptake of c.a. 5.2% which was approximately 2.5 times higher than the maximum uptake of the particles in MCF-7 breast cancer epithelial cells (2.1%). Moreover, NP uptake in RAW 264.7 macrophages was also investigated with different incubation times (0-24 h and 100 μg $mL^{-1}$ of NPs). Results (FIG. 10 diagram D) demonstrate that $HMSiO_2$ NP uptake after incubation for 24 h was almost 3 times higher than when they were incubated for 4 h.

Figure 11:
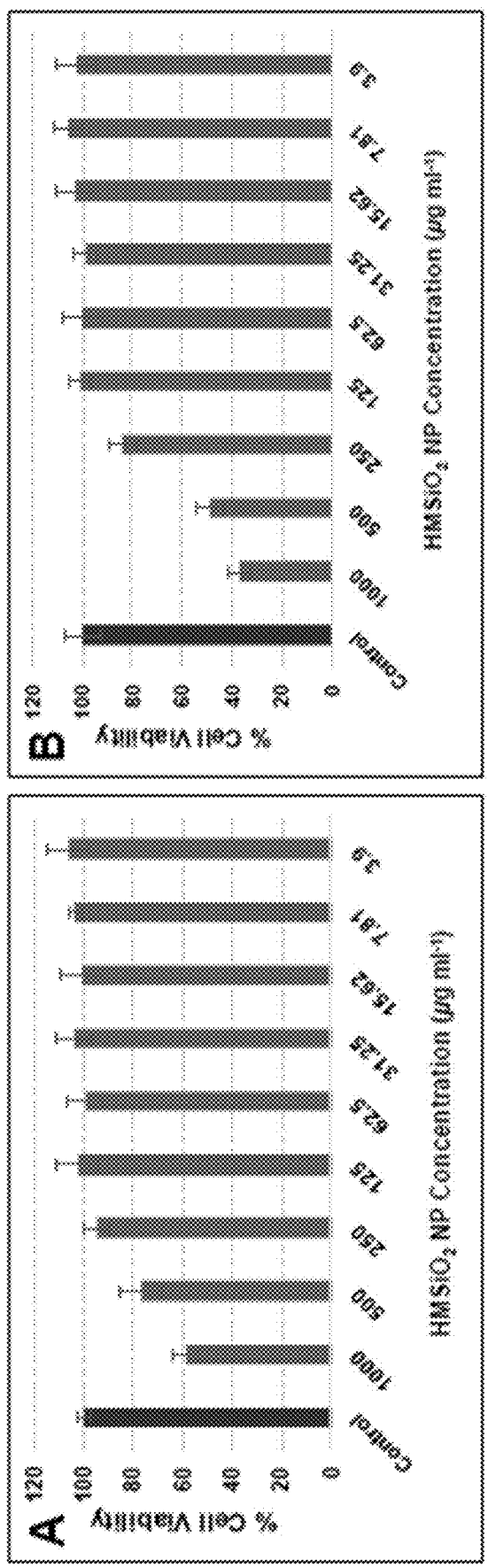
FIG. 11 illustrates graphs depicting cytotoxicity of nanoparticles, according to one implementation.

FIG. 11 illustrates cytotoxicity of GSH-sensitive $HMSiO_2$ nanoparticles in NIH 3T3 fibroblasts after incubation for (FIG. 11 diagram A) 24 hours and (FIG. 11 diagram B) 48 hours. In an embodiment, toxic effects of the particles begin when the cells are treated with nanoparticles in the concentrations between 250 and 1000 microgram per milliliter.

In addition to these cytotoxicity studies conducted in MCF-7 and RAW 264.7 macrophages, we also performed cell toxicity in NIH 3T3 fibroblast cells to see the effect of GSH-sensitive $HMSiO_2$ NPs on normal cells. FIGS. 13A and 13B demonstrate that particles did not show any toxic effects on these cells with the concentrations equal or less than 125 µg mL$^{-1}$. However, with higher concentrations cell viability decreased in a time- and concentration-dependent fashion in which c.a. 41% and 63% reduction was observed in cell viability after 24 and 48 h, respectively when the cells were treated with 1000 µg mL$^{-1}$ of $HMSiO_2$ NPs and c.a. 23% and 51% reduction was seen in cell viability after 24 and 48 h, respectively when the cells were co-cultured with 500 µg mL$^{-1}$ of $HMSiO_2$ NPs.

Cell toxicity of GSH-sensitive and TEOS $HMSiO_2$ NPs, DOX-loaded GSH-sensitive and TEOS $HMSiO_2$ NPs, and free DOX was evaluated in MCF-7 breast cancer epithelial cells after incubation for 24 hours and 48 hours. The results reveal that both GSH-sensitive and TEOS $HMSiO_2$ NPs were almost nontoxic to MCF-7 cells after incubation for 24 hours in the concentration range between 3.9 to 1000 micrograms/milliliter. However, cell toxicity decreased when the cells were treated with a concentration of NPs higher than 126 micrograms/milliliter and incubated for 48 hours. For GSH-sensitive $HMSiO_2$ NPs, this toxic effect started from 250 microgram/milliliter while for TEOS $HMSiO_2$ NPs toxicity was observed with the concentrations equal or greater than 500 microgram/milliliter which possibly results from the accumulation of particles inside these cells and disrupting cell membrane integrity.

Figure 12:
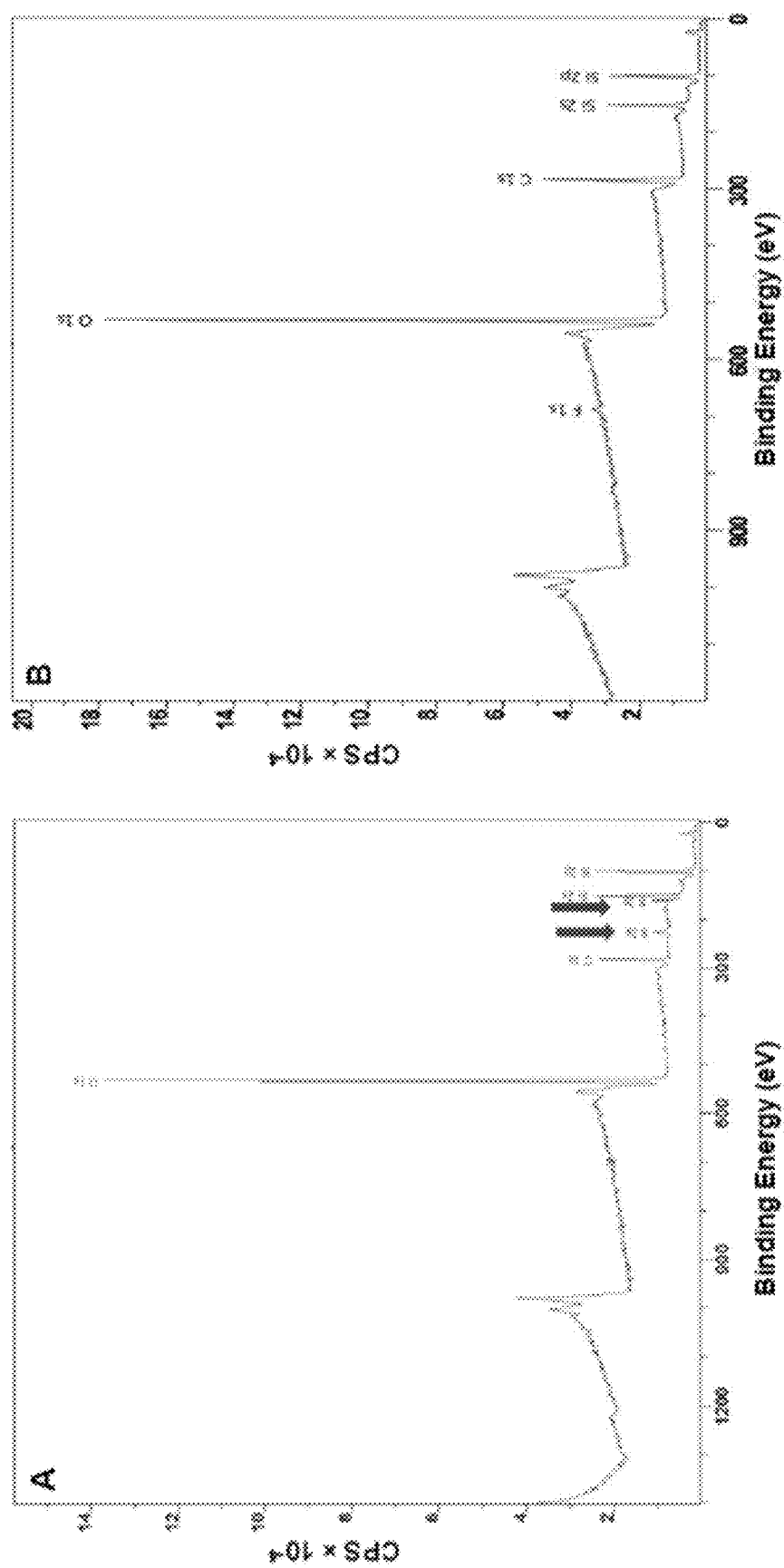
FIG. 12 illustrates data from survey spectra of nanoparticles, according to one implementation.

FIG. 12 illustrates XPS survey spectra of (A) GSH-sensitive $HMSiO_2$ nanoparticles and (B) TEOS $HMSiO_2$ nanoparticles.

ticles at 1402 and mixing tetraethyl orthosilicate (TEOS) and bis[3-(triethoxysilyl)propyl] disulfide (BTESPD) to provide a degradable mesoporous shell at 1404. The method 1400 includes coating each of the plurality of core nanoparticles with the degradable mesoporous shell at 1406. The method 1400 includes etching a majority of each of the plurality of core nanoparticles using an etchant to create a plurality of hollow mesoporous nanoparticle structures each having the mesoporous shell at 1408. The method 1400 is such that the mixing step further comprises a ratio of TEOS to BTESPD of about 1.5:1 to about 4.1 at 1410. The method 1400 is such that at 1412 the concentration of TEOS is at least 10 mM. The method 1400 is such that at 1414 the concentration of BTESPD is at least 1 mM.

Table 1 indicates measurements of GSH-sensitive $HMSiO_2$ NPs, including surface area, total pore area, total pore volume and pore diameter. The surface area is directly related to the presence of interior hollow cavity of the particles. The outer shell of GSH-sensitive $HMSiO_2$ NPs contains approximately 5.5% sulfur in one embodiment.

Table 1 further shows that surface area, total pore area, total pore volume, and pore diameter of GSH-sensitive $HMSiO_2$ NPs were 446±6 m$^2$/g, 173±8.7 m$^2$/g 0.9±0.2 cm$^3$/g, and 2.3±0.5 nm, respectively; while the values for TEOS $HMSiO_2$ NPs were: 523±2 m$^2$/g, 211±11.3 m$^2$/g, 1.1±0.2 cm3 g−1, and 3.1±0.7 nm, respectively. This large surface area is directly related to the presence of interior hollow cavity of these particles which is c.a. 80 m$^2$/g higher than our previous disulfide-based degradable mesoporous SiO2 NPs (366±9 m$^2$/g). X-ray photoelectron spectroscopy (XPS), also known as electron spectroscopy for chemical analysis, is a quantitative technique that measures the elemental composition of the materials within the very top 1-10 nm of the NP's surface. Table 1 indicates that the outer shell of GSH-sensitive $HMSiO_2$ NPs contains c.a. 5.5% sulfur. In addition, XPS survey spectra indicate the presence and absence of S peaks in GSH-sensitive and TEOS $HMSiO_2$ NPs, respectively.

TABLE 2

| Hydrodynamic Diameter (nm) Measured by DLS | | | Zeta Potential (mV) at 25 Centigrade | | | |
|---|---|---|---|---|---|---|
| DI Water | DMEM + 10% FBS | RPMI + 10% FBS | DI Water pH 7.2 | DI Water pH 6 | DMEM + 10% FBS | RPMI + 10% FBS |
| 162 ± 10 | 150 ± 3 | 189 ± 35 | −35 ± 1 | −23 ± 1 | −7 ± 1 | −7 ± 1 |

Figure 13:
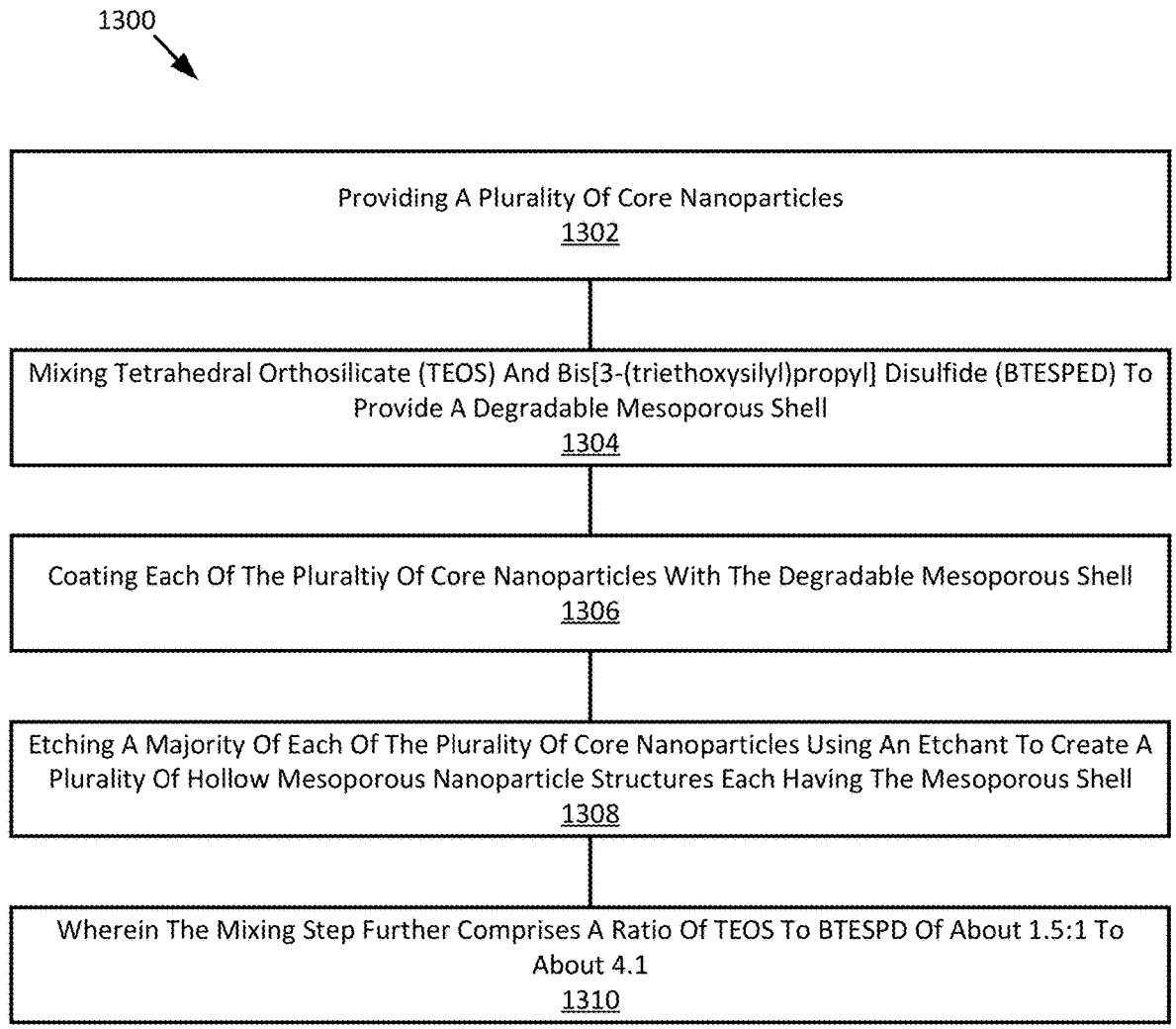
FIG. 13 illustrates a schematic flow chart diagram of a method for producing a biodegradable hollow nanoparticle, according to one implementation.

FIG. 13 illustrates a schematic flow chart diagram of a method 1300 for producing a hollow nanoparticle. The method 1300 includes providing a plurality of core nanoparticles at 1302 and mixing tetraethyl orthosilicate (TEOS) and bis[3-(triethoxysilyl)propyl] disulfide (BTESPD) to provide a degradable mesoporous shell at 1304. The method 1300 includes coating each of the plurality of core nanoparticles with the degradable mesoporous shell at 1306. The method 1300 includes etching a majority of each of the plurality of core nanoparticles using an etchant to create a plurality of hollow mesoporous nanoparticle structures each having the mesoporous shell at 1308. The method 1300 is such that the mixing step further comprises a ratio of TEOS to BTESPD of about 1.5:1 to about 4.1 at 1310.

Figure 14:
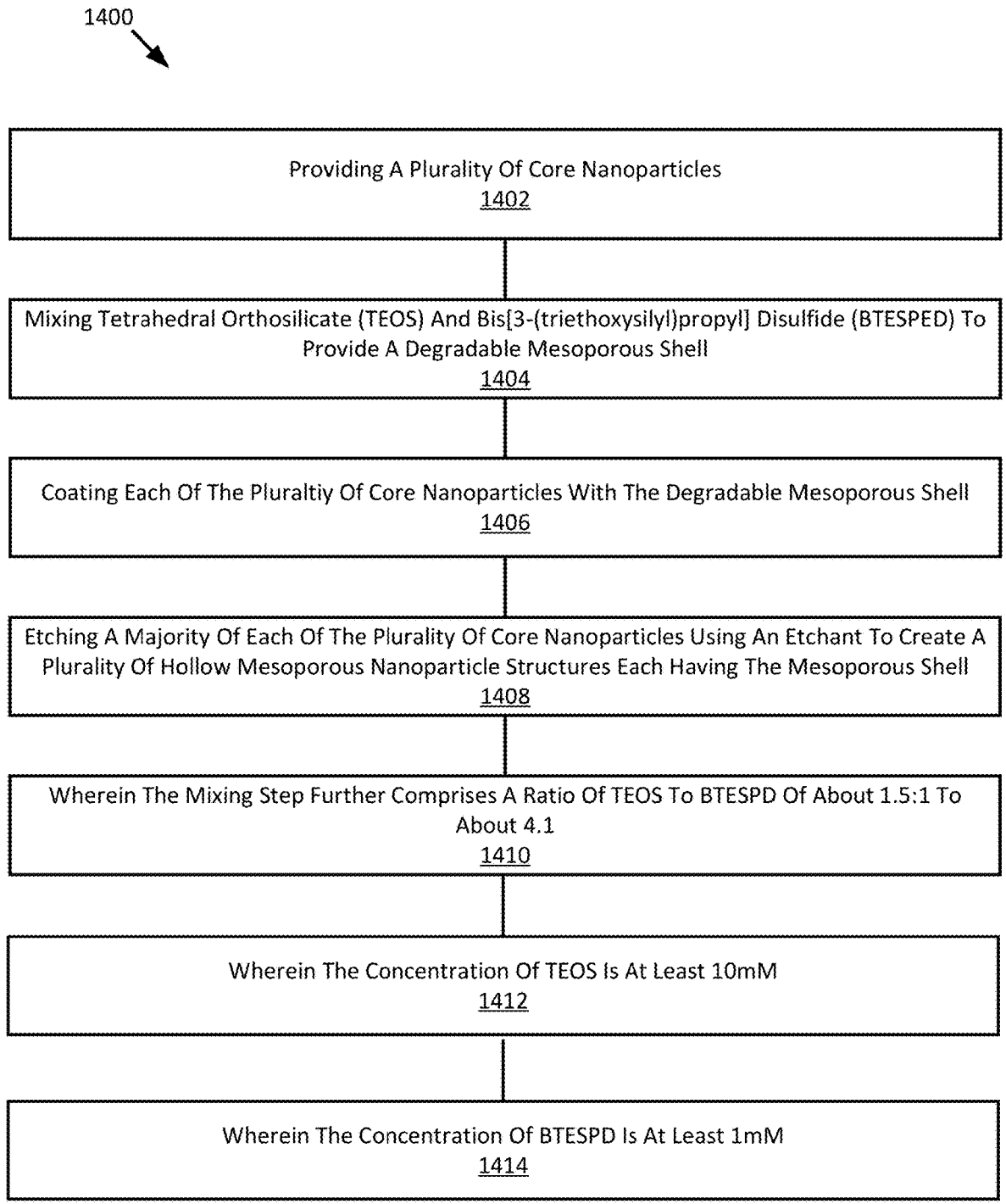
FIG. 14 illustrates a schematic flow chart diagram of a method for producing a biodegradable hollow nanoparticle, according to one implementation.

FIG. 14 illustrates a schematic flow chart diagram of a method 1400 for producing a hollow nanoparticle. The method 1400 includes providing a plurality of core nanopar- Table 2 indicates hydrodynamic diameters of GSH-sensitive $HMSiO_2$ NPs in various media. The average hydrodynamic diameters measured by dynamic light scattering (DLS) were 162±10, 150±3, and 189±35 nm in DI water, DMEM +10% fetal bovine serum (FBS), and RPMI+10% FBS, respectively. The zeta potential measurements were conducted in different media and pH. When GSH-sensitive $HMSiO_2$ NPs are dispersed in DI water, the zeta potential values between −23 and −35 mV indicate the presence of surface silanol (Si—OH) groups. Such groups can become deprotonated in aqueous environments and form Si—O$^-$ which may lead to negative zeta potentials. The zeta potentials values decrease by suspending the particles in media +10% FBS, resulting from high ionic strength of the media via Debye length reduction. By comparison, zeta potential for TEOS $HMSiO_2$ NPs is also measured.

Table 2 further displays hydrodynamic diameters of GSH-sensitive $HMSiO_2$ NPs in various media. The average hydrodynamic diameters measured by dynamic light scattering (DLS) were 162±10, 150±3, and 189±35 nm in deionized (DI) water, DMEM+10% fetal bovine serum (FBS), and RPMI+10% FBS, respectively. Moreover, zeta potential measurements were conducted in different media and pH values. It was shown that zeta potentials were −35±1, −23±1, −7±1, and −7±1 mV in DI water at pH 7.2, DI water at pH 6, DMEM +10% FBS, and RPMI+10% FBS, respectively. When GSH-sensitive $HMSiO_2$ NPs are dispersed in DI water, their zeta potential values between −23 and −35 mV indicates the presence of surface silanol (Si—OH) groups. These groups can become deprotonated in aqueous environments and form Si—O— which lead to negative zeta potentials. These values decrease considerably by suspending the particles in media+10% FBS (zeta potential −7 mV) resulting from high ionic strength of these media via Debye length reduction. For comparison, zeta potential for TEOS $HMSiO_2$ NPs was also measured. The values were −30±2, −21±2, and −10±1 mV in DI water at pH 7.2, DI water at pH 6, and DMEM+10% FBS, respectively.

TABLE 3

| Run | Sodium Carbonate Concentration (mg in 20 mL of DI Water) | NP Concentration (mg in 20 mL of DI Water) | TEOS/DIS Ratio | Stirring Rate (RPM) | Temp. (° C.) | Reaction Time (h) | % Etched NPs | % Broken NPs |
|---|---|---|---|---|---|---|---|---|
| 1 | 500 | 200 | 70/30 | 1200 | 50 | 24 | 10 | 2 |
| 2 | 636 | 200 | 70/30 | 1200 | 50 | 10 | 30 | 1 |
| 3 | 1700 | 100 | 70/30 | 1200 | 50 | 12 | 90 | 60 |
| 4 | 1280 | 200 | 70/30 | 1200 | 80 | 0.5 | 40 | 20 |
| 5 | 2000 | 200 | 70/30 | 1400 | 50 | 8 | 95 | 70 |
| 6 | 636 | 200 | 70/30 | 400 | 50 | 8 | 10 | 0 |
| 7 | 1600 | 200 | 70/30 | 1000 | 50 | 10 | 40 | 10 |
| 8 | 1550 | 200 | 70/30 | 1200 | 50 | 9 | 95 | 1 |
| 9 | 1550 | 200 | 70/30 | 1200 | 50 | 10 | 95 | 1 |
| 10 | 1550 | 200 | 70/30 | 1200 | 50 | 8 | 90 | 1 |
| 11 | 1500 | 200 | 70/30 | 1200 | 50 | 10 | 90 | 2 |
| 12 | 1300 | 200 | 70/30 | 1200 | 50 | 10 | 80 | 2 |
| 13 | 1300 | 200 | 70/30 | 1200 | 50 | 24 | 80 | 10 |
| 14 | 470 | 200 | 70/30 | 1200 | 50 | 9 | 20 | 5 |
| 15 | 1600 | 200 | 70/30 | 1400 | 50 | 8 | 90 | 20 |
| 16 | 1500 | 200 | 50/50 | 1200 | 50 | 10 | 10 | 5 |
| 17 | 1500 | 200 | 25/75 | 1200 | 50 | 10 | 10 | 10 |
| 18 | 3000 | 200 | Just DIS | 1200 | 50 | 10 | 40 | <1 |
| 19 | 1550 | 200 | Just DIS | 1200 | 50 | 10 | 40 | <1 |

TABLE 4

| Run | 10% HF (Stock) | HF Volume Added (μL) | TEOS/DIS Ratio | Stirring Rate (RPM) | Temperature (° C.) | Reaction Time (min or h) | % Etched NPs | % Broken NPs |
|---|---|---|---|---|---|---|---|---|
| 1 | 2.5 mL of Stock in 10 ml of $H_2O$ | 310 | 70/30 | 400 | 50 | 1 min | >95 | 80 |
| 2 | 2.5 mL of Stock in 10 ml of $H_2O$ | 320 | 70/30 | 400 | 50 | 1 min | >95 | 90 |
| 3 | 2.5 mL of Stock in 10 ml of $H_2O$ | 320 | 70/30 | 400 | 50 | 5 min | >95 | 90 |
| 4 | 2.5 mL of Stock in 10 ml of $H_2O$ | 400 | 70/30 | 400 | 50 | 5 min | >95 | 80 |
| 5 | 2.5 mL of Stock in 10 ml of $H_2O$ | 400 | 70/30 | 400 | 50 | 10 min | >95 | 90 |
| 6 | 2.5 mL of Stock in 10 ml of $H_2O$ | 300 | Just DIS | 400 | 50 | 1 min | In each particle half etching was observed (rattle-type Particles) | 1< |
| 7 | 2.5 mL of Stock in 10 ml of $H_2O$ | 300 | Just DIS | 400 | 50 | 30 min | 5 | 1< |
| 8 | 2.5 mL of Stock in 10 ml of $H_2O$ | 300 | Just DIS | 400 | 50 | 1 h | 5 | 1< |
| 9 | 2.5 mL of Stock in 10 ml of $H_2O$ | 300 | Just DIS | 400 | 50 | 4 h | 10 | 1 |
| 10 | 2.5 mL of Stock in 10 ml of $H_2O$ | 300 | Just DIS | 400 | 50 | 10 h | 50 | 1 |

Table 3 illustrates synthesis parameters for a plurality of runs.

Table 4 illustrates synthesis parameters for a plurality of runs.

In an embodiment of the disclosure, transmission electron microscopy (TEM) indicated that the fabricated $HMSiO_2$ NPs had an average diameter of 130±5 nm. Thermogravimetric analysis (TGA) revealed that GSH-sensitive particles had approximately 5.3% more weight loss than TEOS $HMSiO_2$ NPs which is attributed to the disulfide containing organosilicon matter. Zeta potential of these redox-responsive particles was −23±1 mV at pH 6 in deionized (DI) water. Nitrogen adsorption-desorption isotherm revealed that the surface area of these hollow mesoporous nanoreservoirs was roughly 446±6 m2/g and the average diameter of the pores was 2.3±0.5 nm. TEM images suggest that the nanoparticles started to degrade from Day 1. These hollow silica nanobubbles showed high loading capacity for DOX (8.9±0.5%) which is directly proportional to the large voids existing in the hollow structures. Approximately 58% of the incorporated DOX released within 14 days in phosphate buffered saline (PBS) at pH 6 and 10 mM GSH mimicking intracellular tumor microenvironment while release from TEOS $HMSiO_2$ NPs was only c.a. 18%. The uptake of these hollow nanospheres in MCF-7 cells and RAW 264.7 macrophages was evaluated using TEM and confocal microscopy in which the nanospheres were shown to accumulate in the endolysosomal compartments after incubation for 24 h with the maximum uptake of c.a. 2.1±0.3% and 5.2±0.4%, respectively. These values revealed that there is a threshold for $HMSiO_2$ NPs uptake based on the cells. Cytotoxicity of the nanospheres was investigated using CCK-8 assay. Results indicate that the intact hollow particles (both GSH-sensitive and TEOS $HMSiO_2$ NPs) were nontoxic to MCF-7 cells after incubation for 24 h within the concentration range of 0-1000 µg/ml. However, DOX-loaded GSH-sensitive nanospheres containing 6 µg/ml of DOX killed c.a. 51% of the cancer cells after 24 h while TEOS $HMSiO_2$ NPs killed c.a. 80% which was statistically significant.

In an embodiment of the disclosure, a biodegradable hollow SiO2 NP is produced using cetyltrimethylammonium bromide (CTAB)-based methods for synthesizing spherical porous and nonporous particles. In such an embodiment, a high temperature and a high stirring rate is used while adding tetraethyl orthosilicate and bis(triethoxysilylpropyl) dilsufide to a CTAB solution comprising 2M sodium hydroxide. In an embodiment, the solution is stirred for several hours.

In an embodiment of the disclosure a GSH-sensitive biodegradable hollow mesoporous silica nanoparticle is provided. The nanoparticle has an average diameter of approximately 130 nm. The nanoparticle is size-tunable in terms of internal hollow cavity and shell thickness and can incorporate a substantial number of active agents, including for example DOX. The nanoparticle can degrade from the outer shell containing disulfide bonds in the presence of intracellular concentrations of GSH. In an embodiment, an active agent such as DOX is released within two weeks in the presence of 10 mM of GSH at pH 6 resembling intratumoral microenvironment.

In an embodiment of the disclosure, a GSH-sensitive and TEOS $HMSiO_2$ NP is synthesized by the following parameter. 100 nm of dense Stöber core NPs are prepared as follows: 1700 mmol of absolute ethanol, 180 mmol of DI water, and 200 mmol of ammonium hydroxide mixed in a flask under a stirring rate of 400 rpm for 10 min. 18 mmol of TEOS is added dropwise and the reaction is left under stirring for 24 hours at room temperature. The synthesized NPs are precipitated by centrifugation at 15,000 rpm for 20 min., washed with DI water and ethanol, and stored in DI water for further use. The synthesized Stöber NPs are coated with surfactant-based mesoporous silica shell (core-shell NPs). This step includes providing 1300 mmol of DI water, 60 mmol of absolute ethanol, 0.2 mmol of TEA, 0.16 mmol of CTAB, and 10 mL of stock Stöber suspension, and mixing at 80 Centigrade under a stirring rate of 600 rpm for 50 minutes. The reaction is allowed to stir for four hours. For preparing a TEOS shell, 0.65 mmol of TEOS is added to the suspension and the reaction is allowed to stir for four hours. The hollow cavity and the shell thickness are tunable depending on the amount of the precursor used in the formation of dense Stöber core and mesoporous coating procedure (the ratio of TEOS to BTESPD). The mesoporous coated Stöber NPs are precipitated by centrifugation at 15,000 rpm for 20 min. and washed twice with DI water and ethanol 95%. The $HMSiO_2$ NPs are formed via etching with sodium carbonate.

In an embodiment of the disclosure, two nonporous nanoparticles are synthesized. The two nanoparticles comprise a diameter of 120±20 nm and 330±15 nm. In an embodiment, mesoporous nanoparticles are provided having a diameter of 60±15 nm and 120±30 nm. The mesoporous nanoparticles have a surface area of about 614 m²/g for the 60±15nm particle and about 366 m²/g for the 120±30 nm particle. The nonporous particles have a surface area of about 21 m²/g for the 330±15 nm particle, and about 54 m²/g for the 120±20 nm particle. In an embodiment, the mesoporous nanoparticles are prone to degrading faster than the nonporous nanoparticles.

The disclosure relates to the fabrication and characterization of GSH-sensitive biodegradable mesoporous silica nanoparticles with an average diameter of about 130 nm. These particles were size-tunable in terms of internal hollow cavity and shell thickness and can incorporate substantial number of active agents like DOX (~8.9%). We have shown that these uniform nanoparticles can degrade from the outer shell containing disulfide bonds in the presence of intracellular concentrations of GSH (~10 mM). Release study suggests that ~60% of DOX releases within 2 weeks in the presence of 10 mM of GSH at pH 6 resembling intratumoral microenvironment.

The examples and disclosures herein were conducted using a plurality of compounds, solvents, and reactants. The following compounds are disclosed: aminopropyltriethoxysilane (APTES, ≥98.0%), triethylamine (TEA, ≥99.0%), cetyltrimethylammonium bromide (CTAB, ≥99.0%), tetraethyl orthosilicate (TEOS, ≥99.0% GC), Triton™ X-100, bisbenzimide Hoechst No. 33342, fetal bovine serum (FBS), and glutathione (GSH). Dulbecco's Modified Eagle Medium (DMEM), TrypLE™, fluorescein isothiocyanate (FITC), and LysoTracker™ Deep Red were received from Thermo Fisher Scientific (Grand Island, N.Y., USA). Bis[3-(triethoxysilyl)propyl] disulfide (BTESPD, 90.0%) was purchased from Gelest, Inc. (Morrisville, Pa., USA). Doxorubicin hydrochloride salt (DOX, >99.0%) was acquired from LC Laboratories (Woburn, Mass., USA). Sodium carbonate (Na2CO3, anhydrous, granular, ≥99.5%) was received from Mallinckrodt Chemicals (Phillipsburg, N.J., USA). Sodium Chloride High Purity Grade (NaCl, 99.9%) was purchased from AMRESCO® (Solon, Ohio, USA). Roswell Park Memorial Institute-1640 (RPMI-1640) medium, hydrochloric acid ACS Grade BDH (36.5-38.0%), and phosphate buffered saline (PBS) Biotechnology Grade tablets were received from VWR (Radnor, Pa., USA). Absolute ethanol (200 proof) and ethanol 95% were purchased from Decon Labs, Inc. Trypan Blue Stain 0.4% was obtained from Invitrogen (Carlsbad, Calif., USA). Hydrofluoric acid (HF, 48.0%) and ammonium hydroxide (NH4OH, 28.0-30.0% as NH3) were received from EMD Millipore Corporation (Billerica, Mass., USA). RAW 264.7 macrophages (ATCC® TIB-71™), MCF-7 breast cancer cells (ATCC® HTB-22™), and NIH 3T3 (ATCC® CRL-1658™) fibroblasts were obtained from American Type Culture Collection (ATCC, Manassas, Va., USA). CCK-8 cytotoxicity assay kit was received from Dojindo (Rockville, Md., USA). All materials were used as received without further purification.

The following pertains to an example embodiment of the disclosure. To synthesize the GHS-Sensitive hollow silica nanoparticle. First, 100 nm dense Stöber core NPs were prepared as follow: 1700 mmol of absolute ethanol, 180 mmol of DI water, and 200 mmol of ammonium hydroxide were mixed in a flask under stirring rate of 400 rpm for 10 min. Then, 18 mmol of TEOS was added dropwise and the reaction was left under stirring for 24 h at room temperature. Next, the synthesized NPs (900 mg) were precipitated by centrifugation using Sorvall® RC-5B Refrigerated Superspeed Centrifuge (Du Pont Instruments Ltd., Wilmington, Del., USA) at 15,000 rpm for 20 min, washed thoroughly with DI water and ethanol 95%, and stored in 50 mL of DI water for further use (stock Stöber suspension: 18 mg mL$^{-1}$). It is to be understood that the silica core particles (Stöber particles) may have a diameter within a range of about 600 nanometers to about 30 nanometers without departing from the scope of the disclosure.

Second, the synthesized Stöber NPs were coated with surfactant-based mesoporous silica shell (core-shell NPs). For this step, 1300 mmol of DI water, 60 mmol of absolute ethanol, 0.2 mmol of TEA, 0.16 mmol of CTAB, and 10 mL of the stock Stöber suspension were mixed in a 100-mL round bottom flask at 80° C. under stirring rate of 600 rpm for 50 min. Afterward, for preparing GSH-sensitive shell, stirring rate was increased to 1400 rpm, and 0.42 mmol of TEOS and 0.08 mmol of BTESPD were added simultaneously. Then, the reaction was allowed to stir for 4 h. For preparing TEOS shell, 0.65 mmol of TEOS was added to the suspension and the reaction was allowed to stir for 4 h at 80° C. and 1400 rpm. As discussed, the hollow cavity (~80-250 nm) and the shell thickness (~10-30 nm) are tunable depending on the amount of the precursor used in the formation of a dense Stöber core and mesoporous coating procedure (ratio of TEOS to BTESPD), respectively. Next, the mesoporous coated Stöber NPs were precipitated by centrifugation at 15,000 rpm for 20 min and washed twice with DI water and ethanol 95%.

Third, HMSiO$_2$ NPs were formed via etching with sodium carbonate due to structural/compositional differences between the core and the shell. So, for fabricating GSH-sensitive and TEOS HMSiO$_2$ NPs, 15 and 12.5 mmol of sodium carbonate, respectively were dissolved in 10 mL of DI water in a 100-mL round bottom flask at 50° C. under stirring rate of 600 rpm for 30 min. The obtained core-shell NPs were dispersed in 10 mL of DI water and sonicated for 30 min. Then, stirring rate was increased to 1200 rpm and the NPs suspension was added to sodium carbonate solution. The reaction was kept under stirring for 10 h. lastly, the product was washed thrice with water/ethanol 95% mixture, suspended in acidic ethanol (1 mL HCl 36.5% in 30 mL absolute ethanol), and heated to 80° C. under reflux for 6 h to remove the surfactant. Acidic ethanol washing step was repeated twice and HMSiO$_2$ NPs were then stored in absolute ethanol for further use.

Size and morphology of the nanoparticles were investigated by electron microscopy methods. Transmission electron microscopy (TEM) and scanning electron microscopy (SEM) images were taken by FEI Tecnai™ 12 transmission electron microscope (Hillsboro, Oreg., USA) operating at 120 kV and FEI Quanta 600F scanning electron microscope (Hillsboro, Oreg., USA) operating at 20 kV, respectively. Hydrodynamic diameter and zeta potential measurements were studied by dynamic light scattering (DLS) in a Malvern Instruments Zetasizer Nano ZS (Malvern Instruments Ltd., Worcestershire, UK). Measurements were performed in triplicate. Thermogravimetric analyses (TGA) were conducted using a TA Instruments hi-res TGA 2950 Thermogravimetric Analyzer (New Castle, Del., USA). All TGA experiments were studied under N2 atmosphere from 35 to 800° C. at a heating rate of 20° C./min. Nitrogen adsorption-desorption isotherm analyses were conducted at −196° C. on a Micromeritics ASAP 2020 (Norcross, Ga., USA) for measuring surface area and pore size. All samples were dried at 100° C. overnight prior to analysis. X-ray diffraction (XRD) patterns of all nanoparticles were investigated on a Bruker D2 Phaser X-ray diffractometer (Bruker AXS, Madison, Wis., USA) using Cu Ka radiation ($\lambda$=0.1542 nm) at 45 kV and 40 mA. The XRD spectra were recorded at a scanning speed of 0.01 deg/s, with a step size of 0.02° in a 2-theta scattering angle and in a range of 2-8. Scanning transmission electron microscopy (STEM) images and spectra of the nanoparticles were obtained on JEOL JEM-2800 (Akishima, Tokyo, Japan) scanning transmission electron microscope with dual energy dispersive X-ray spectrometer (EDS) detectors at an electron beam energy of 200 kV. Sample preparation was done by drop casting the nanoparticles on a carbon coated TEM grid. Pore volume and pore size distributions were acquired from an adsorption branch by using the Barrett-Joyner-Halenda (BJH) method. The Brunauer-Emmett-Teller (BET) specific surface areas were measured via adsorption data at P/P0=0.05-0.20. X-ray photoelectron spectroscopy (XPS) analyses of the nanoparticles were performed by Axis Ultra DLD instrument (Kratos Analytical, Manchester, UK). For analyses, the samples were mounted on a C tape and pumped overnight in the load lock before introduction into the analysis chamber. A mono Al source was employed. Survey scans were collected with a pass energy of 160 eV, step size of 1 eV, and dwell time of 200 ms. High resolution region scans were collected with a pass energy of 40 eV, 0.1 eV step size, and 400 ms dwell time. Data were processed using CASA XPS software.

Degradation of GSH-sensitive HMSiO$_2$ NPs (50 µg mL$^{-1}$) was evaluated mimicking intracellular and extracellular GSH concentrations (10 mM and 10 µM, respectively) in DI water at pH 6 and under constant shaking (160 rpm; Amerex Instruments Inc., Concord, Calif., USA) at 37° C. At predetermined time points (0, 6 h, 1, 3, and 7 days), samples were collected for TEM analysis. Next, water suspensions containing nanoparticles were drop-casted onto Formvar coated Cu grids and allowed to dry prior to visualization using FEI Tecnai T12 operating at 120 kV.

Cytotoxicity of the intact GSH-sensitive HMSiO$_2$ NPs, TEOS HMSiO$_2$ NPs, DOX-loaded GSH-sensitive HMSiO$_2$ NPs, DOX-loaded TEOS HMSiO$_2$ NPs, and free DOX was evaluated in MCF-7 breast cancer epithelial cells. Cells were cultured at 37° C. in 5% CO2 in DMEM with 10% FBS. Then, the cells were stained using Trypan Blue Stain 0.4% and read by Invitrogen Countess™ automated cell counter (Thermo Fisher Scientific Corporation, Grand Island, N.Y., USA). For the cytotoxicity evaluation, cells were seeded onto 96-well plates with the density of 4,000 cells/well and incubated to grow for 48 h. After 48 h, the cells were washed with PBS. Fresh media containing 10% FBS was then added (120 μL) with varying nanoparticle concentrations ranging from 0 to 1,000 μg mL$^{-1}$. Wells with media or Triton™ X-100 (without nanoparticles) were used as negative or positive controls, respectively. The cells were then incubated for another 24 and 48 h, the media was aspirated, and the cells were washed twice with PBS. Cell viability was determined using CCK-8 cytotoxicity assay kit according to an established protocol and absorbance was measured at 450 nm with SpectraMax® M2 microplate reader. Assays were performed at least in triplicate.

Cytotoxicity of the intact GSH-sensitive HMSiO$_2$ NPs was also evaluated in RAW 264.7 macrophages and NIH 3T3 fibroblasts. Again, cells were cultured at 37° C. in 5% CO2 in RPMI-1640 and DMEM (for RAW 264.7 macrophages and NIH 3T3, respectively) with 10% FBS and seeded onto 96-well plates with the density of 4,000 cells/well and incubated to grow for 48 h. After, the cells were washed with PBS. Fresh media containing 10% FBS was then added with varying nanoparticle concentrations ranging from 0 to 1,000 μg mL$^{-1}$. The cells were then incubated for another 24 and 48 h, the media was aspirated, and the cells were washed twice with PBS. Cell viability was measured using CCK-8 cytotoxicity assay kit at 450 nm. Assays were performed at least in triplicate.

In this embodiment, DOX was used as an anticancer drug model. DOX was incorporated in GSH-sensitive and TEOS HMSiO$_2$ NPs according to the following procedure: 7.5 mg of DOX and 10 mg of HMSiO$_2$ NPs were mixed in 7.5 mL of DI water. The reaction was kept under stirring (1000 rpm) for 24 h at room temperature. After 24 h, DOX-loaded HMSiO$_2$ NPs were precipitated by centrifugation at 15,000 rpm for 20 min and washed five times with DI water to remove free Dox or the DOX attached on the surface of these NPs. DOX loading capacity in HMSiO$_2$ NPs was then calculated using UV-Vis spectroscopy at 480 nm based on DOX calibration curve plotted in the range of concentrations between 3.9 and 250 μg mL$^{-1}$.

For release study, DOX-loaded GSH-sensitive HMSiO$_2$ NPs (2 mg) were dispersed in 10 mL of PBS at pH 6 containing 2 and 10 mM GSH and in 10 mL of PBS at pH 7.2 containing 10 mM GSH. Vials with NPs in PBS at pH 6 (without GSH) were used as Controls. For comparison study, DOX-loaded TEOS HMSiO$_2$ NPs (2 mg) were dispersed in 10 mL of PBS pH 6. Subsequently, the suspension was kept under constant shaking (160 rpm) at 37° C. Next, equal aliquots were taken out at specific time points (0, 2, 4, 6, 12, 24, 48, 72, 120, 168, and 366 h), centrifuged at 13,000 rpm for 20 min, and the supernatants were utilized to measure the amount of the released DOX from the NPs with excitation wavelength at 480 nm. The concentrations were all measured using DOX standard curve. All measurements were performed at least in triplicate.

In the disclosure, data are articulated as mean±standard deviations (SD) for at least three separate experiments. The difference between multiple groups was studied using analysis of variance (ANOVA). For comparison between two groups, t-test was applied. The difference compared to control was considered significant at Pvalue<0.05.

EXAMPLES

The following examples pertain to further embodiments.

Example 1 is a method of preparing a hollow mesoporous nanoparticle. The method includes providing a plurality of core nanoparticles and mixing tetraethyl orthosilicate (TEOS) and bis[3-(triethoxysilyl)propyl] disulfide (BTESPD) to provide a degradable mesoporous shell. The method includes coating each of the plurality of core nanoparticles with the degradable mesoporous shell. The method includes etching a majority of each of the plurality of core nanoparticles using an etchant to create a plurality of hollow mesoporous nanoparticle structures each having the mesoporous shell. The method is such that the mixing step further comprises a range of about 1% TEOS to 99% BTESPD. In an embodiment, the range of about 80% TEOS to about 20% BTESPD.

Example 2 is a method as in Example 1, wherein the surfactant-based mesoporous shell comprises a thickness ranging between about five nanometers to about one-hundred nanometers.

Example 3 is a method as in any of Examples 1-2, wherein the concentration of TEOS is at least about 10 mM.

Example 4 is a method as in any of Examples 1-3, wherein the concentration of BTESPD is at least about 1 mM.

Example 5 is a method as in any of Examples 1-4, wherein etching further comprises stirring at a rate of about 300 revolutions per minute to about 2000 revolutions per minute.

Example 6 is a method as in any of Examples 1-5, wherein etching further comprises stirring at a rate of 1000 revolutions per minute or greater.

Example 7 is a method as in any of Examples 1-6, wherein the method further comprises an etching reaction time of about 0.5 hours to about 24 hours based on reaction conditions and relative amounts of TEOS and BTESPD.

Example 8 is a method as in any of Examples 1-7, wherein the method further comprises an etching reaction time of about 8 hours to about 12 hours based on reaction conditions and relative amounts of TEOS and BTESPD.

Example 9 is a method as in any of Examples 1-8, wherein the etchant is sodium carbonate and the concentration of sodium carbonate is about 50 mg/ml to about 200 mg/ml.

Example 10 is a method as in any of Examples 1-9, wherein the etchant is sodium chloride with hydrochloric acid; wherein a mixture of sodium chloride with hydrochloric acid is about 1mL, 0.1 M hydrochloric acid and 0.06g sodium chloride in 15 mL of deionized water.

Example 11 is a method as in any of Examples 1-10, wherein the etching reaction temperature is about 25 degrees to about 100 degrees Celsius.

Example 12 is a method as in any of Examples 1-11, wherein the etching reaction temperature is about 50 degrees Celsius.

Example 13 is a method as in any of Examples 1-12, wherein the plurality of core nanoparticles comprises Stöber nanoparticles.

Example 14 is a method as in any of Examples 1-13, wherein the plurality of core nanoparticles comprises a polymer.

Example 15 is a method as in any of Examples 1-14, wherein the polymer is polylactic acid (PLA).

Example 16 is a method as in any of Examples 1-15, wherein the polymer is polylactic-co-glycolic acid (PLGA).

Example 17 is a method as in any of Examples 1-16, wherein the etchant is a strong base or a strong acid.

Example 18 is a method as in any of Examples 1-17, wherein the strong base comprises a pH greater than or equal to 12.

Example 19 is a method as in any of Examples 1-18, wherein the strong acid comprises a pH of less than or equal to 2.

Example 20 is a method as in any of Examples 1-19, wherein the etchant is hydrofluoric acid and the concentration of hydrofluoric acid is within a range of about 5wt % to about 20wt %.

Example 21 is a method as in any of Examples 1-20, wherein the mesoporous shell comprises a plurality of pores, wherein the size of the pores range between about 2 nanometers and about 4 nanometers.

Example 22 is a method as in any of Examples 1-21, wherein the degradability of the mesoporous shell is dependent on the glutathione (GSH) concentration in a living cell.

Example 23 is a method as in any of Examples 1-22, wherein the mesoporous shell is surfactant based and comprises silica and disulfide bonds that are sensitive to glutathione (GSH).

Example 24 is a method as in any of Examples 1-23, wherein the mixing step further comprises a ratio of TEOS to BTESPD of about 2:1 to about 2.25:1.

Example 25 is a method of preparing a hollow mesoporous nanoparticle. The method includes providing a plurality of core nanoparticles and mixing tetraethyl orthosilicate (TEOS) and bis[3-(triethoxysilyl)propyl] disulfide (BTESPD) to provide a degradable mesoporous shell. The method includes coating each of the plurality of core nanoparticles with the degradable mesoporous shell. The method includes etching a majority of each of the plurality of core nanoparticles using an etchant to create a plurality of hollow mesoporous nanoparticle structures each having the mesoporous shell. The method is such that the mixing step further comprises a ratio of TEOS to BTESPD of about 1.5:1 to about 4:1. The method is such that the concentration of TEOS is at least about 10 mM. The method is such that the concentration of BTESPD is at least about 1 mM.

Example 26 is a method of synthesizing a hollow nanoparticle. The method includes providing a plurality of silica core particles. Each of the plurality of silica core particles comprise a diameter within a range of about 600 nanometers to about 30 nanometers. The method includes synthesizing a mesoporous silica shell around the plurality of silica core particles forming a plurality of mesoporous coated silica core particles. The method further etching the plurality of mesoporous coated silica core particles with an aqueous solution of sodium carbonate and water to remove the silica core particle from the plurality of mesoporous coated silica core particles forming a plurality of hollow mesoporous particles. The method also includes diffusing a payload into the plurality of hollow mesoporous particles in an aqueous solution.

Example 27 is a method as in any of Examples 1-26, wherein the aqueous solution comprises a concentration range of about 650 milligrams to about 2000 milligrams of sodium carbonate per about 10 milliliters of deionized water.

Example 28 is a method as in any of Examples 1-27, wherein the solution comprises a concentration range of about 1450 milligrams to about 1600 milligrams of sodium carbonate per about 10 milliliters of deionized water.

Example 29 is a method as in any of Examples 1-28, wherein the concentration is about 1540 milligrams of sodium carbonate per about 10 milliliters of deionized water.

Example 30 is a method as in any of Examples 1-29, wherein etching occurs at a temperature range of about 25 degrees Celsius to about 80 degrees Celsius.

Example 31 is a method as in any of Examples 1-30, wherein etching occurs at a temperature of about 50 degrees Celsius.

Example 32 is a method as in any of Examples 1-31, wherein etching is performed between a time range of about eight hours to about nine hours.

Example 33 is a method as in any of Examples 1-32, wherein etching is performed between a time range of about three hours to about twenty-four hours.

Example 34 is a method as in any of Examples 1-33, wherein etching is performed between a time range of about eight hours to about nine hours.

Example 35 is a method as in any of Examples 1-34, wherein the mesoporous silica shell comprises a surfactant.

Example 36 is a method as in any of Examples 1-35, wherein synthesizing the mesoporous silica shell around the plurality of silica core particles comprises coating the plurality of silica core particles with bis[3-(triethoxysilyl)propyl] disulfide (BTESPD).

Example 37 is a method as in any of Examples 1-36, wherein synthesizing the mesoporous silica shell around the plurality of silica core particles further comprises coating the plurality of silica core particles with tetraethyl orthosilicate (TEOS).

Example 38 is a method as in any of Examples 1-37, wherein synthesizing the mesoporous silica shell around the plurality of silica core particles comprises coating the plurality of silica core particles with bis[3-(triethoxysilyl)propyl] disulfide (BTESPD); wherein the ratio of TEOS to BTESPD is within a range of about 1% TEOS to about 99% BTESPD to 80% TEOS to about 20% BTESPD.

Example 39 is a method as in any of Examples 1-38, wherein synthesizing the mesoporous silica shell around the plurality of silica core particles further comprises coating with ethanol, water, triethylamine, and cetyltrimethylammonium bromide.

Example 40 is a method as in any of Examples 1-39, wherein etching the plurality of mesoporous coated silica core particles with the aqueous solution comprises stirring during the entire etching process at a rate of about 400 revolutions per minute (RPM) to about 1600 revolutions per minute (RPM).

Example 41 is a method as in any of Examples 1-40, wherein diffusing the payload into the plurality of hollow mesoporous particles results in a plurality of payload filled hollow mesoporous particles and a plurality of non-payload filled hollow mesoporous particles, wherein about 90% or greater of the plurality of hollow mesoporous particles are payload filled hollow mesoporous particles.

Example 42 is a method as in any of Examples 1-41, wherein the mesoporous silica shell comprises a thickness, wherein the thickness of the mesoporous silica shell determines a rate of release of the payload.

Example 43 is a method as in any of Examples 1-42, wherein the rate of release of the payload is slowed as the mesoporous silica shell thickness increases.

Example 44 is a method as in any of Examples 1-43, wherein the plurality of silica core particles are synthesized by: adding about 100 milliliters of 100% ethanol into about 2.8 milliliters of deionized water creating an ethanol-water solution in a first container; adding about 3.6 milliliters of ammonium hydroxide to the ethanol-water solution; stirring at a rate of about 400 revolutions per minute (RPM) at a temperature range of about 16 degrees Celsius to about 24 Celsius for about ten minutes; adding about 3.5 milliliters of tetraethyl orthosilicate (TEOS) and sealing the first container; and stirring a resulting solution at about 400 revolutions per minute (RPM) for about twenty-four hours.

Example 45 is a method as in any of Examples 1-44, wherein synthesizing the mesoporous silica shell around the plurality of silica core particles comprises: adding about 2.727 milliliters of 100% ethanol, about 27 microliters triethylamine, about 70 milligrams cetyltrimethylammonium bromide, and about 20 milliliters of deionized water in a second container; stirring at a rate of about 600 revolutions per minute (RPM) at a temperate of about 80 degrees Celsius for about 30 minutes; adding about 10 milliliters of the plurality of silica core particles from the first container into the second container and stirring for about 15 minutes; increasing the stirring rate to about 1400 revolutions per minute (RPM) while simultaneously adding about 87.5 microliters of TEOS and about 37.5 microliters of BTESPD and stirring for another 3 hours.

Example 46 is a method as in any of Examples 1-45, wherein etching the plurality of mesoporous coated silica core particles comprises: dissolving about 1540 milligrams of sodium carbonate to about 10 milliliters of deionized water in a third container; stirring the resulting solution at a temperature of about 50 degrees Celsius at a rate of about 600 revolutions per minute (RPM) for about one hour; increase the stirring rate to about 1200 revolutions per minute (RPM); adding 10 milliliters of the plurality of mesoporous coated silica core particles from the second container into the third container; and stirring for a time range of about eight hours to about nine hours.

The foregoing description has been presented for the purposes of illustration and description. It is not intended to be exhaustive or to limit the disclosure to the precise form disclosed. Many modifications and variations are possible in light of the above teaching. Further, it should be noted that any or all of the aforementioned alternate implementations may be used in any combination desired to form additional hybrid implementations of the disclosure.

Further, although specific implementations of the disclosure have been described and illustrated, the disclosure is not to be limited to the specific forms or arrangements of parts so described and illustrated. The scope of the disclosure is to be defined by the claims appended hereto, any future claims submitted here and in different applications, and their equivalents.

In the foregoing Detailed Description, various features of the disclosure are grouped together in a single implementation for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed implementation. Thus, the following claims are hereby incorporated into this Detailed Description by this reference, with each claim standing on its own as a separate implementation of the disclosure.

It is to be understood that the above-described arrangements are only illustrative of the application of the principles of the disclosure. Numerous modifications and alternative arrangements may be devised by those skilled in the art without departing from the spirit and scope of the disclosure and the appended claims are intended to cover such modifications and arrangements. Thus, while the disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A method of synthesizing a hollow nanoparticle comprising:
   providing a plurality of silica core particles, wherein each of the plurality of silica core particles comprise a diameter within a range of about 600 nanometers to about 30 nanometers;
   coating the plurality of silica core particles with a surfactant-based mesoporous shell to form a plurality of mesoporous coated silica core particles, wherein coating the plurality of silica core particles comprises providing each of tetraethyl orthosilicate (TEOS), and bis[3-(triethoxysilyl)propyl] disulfide (BTESPD), deionized water, ethanol, triethylamine (TEA), and cetyltrimethylammonium bromide (CTAB);
   etching the plurality of mesoporous coated silica core particles with an aqueous solution of sodium carbonate and water to remove the silica core particle from the plurality of mesoporous coated silica core particles forming a plurality of hollow mesoporous particles; and
   diffusing a payload into the plurality of hollow mesoporous particles in an aqueous solution.

2. The method of claim 1, wherein the aqueous solution comprises a concentration range of about 650 milligrams to about 2000 milligrams of sodium carbonate per about 10 milliliters of deionized water.

3. The method of claim 1, wherein the aqueous solution comprises a concentration range of about 1450 milligrams to about 1600 milligrams of sodium carbonate per about 10 milliliters of deionized water.

4. The method of claim 3, wherein the concentration range of the aqueous solution is about 1540 milligrams of sodium carbonate per about 10 milliliters of deionized water.

5. The method of claim 1, wherein etching the plurality of mesoporous coated silica core particles occurs at a temperature range of about 25 degrees Celsius to about 80 degrees Celsius.

6. The method of claim 1, wherein etching the plurality of mesoporous coated silica core particles occurs at a temperature of about 50 degrees Celsius.

7. The method of claim 1, wherein etching the plurality of mesoporous coated silica core particles is performed between a time range of about eight hours to about nine hours.

8. The method of claim 1, wherein etching the plurality of mesoporous coated silica core particles is performed between a time range of about three hours to about twenty-four hours.

9. The method of claim 1, wherein etching the plurality of mesoporous coated silica core particles is performed between a time range of about eight hours to about nine hours.

10. The method of claim 1, wherein the surfactant-based mesoporous shell comprises one or more of a Si—O—Si—C—C—C—S—S—C—C—C—Si—O—Si bond or a Si—O—Si bond coated on a surface of the plurality of silica core particles.

11. The method of claim 1, wherein coating the plurality of silica core particles with the surfactant-based mesoporous shell comprises coating Si—O—Si—C—C—C—S—S—C—C—C—Si—O—Si and Si—O—Si bonds on surfaces of the plurality of silica core particles using TEOS and BTESPD precursors.

12. The method of claim 1, wherein coating the plurality of silica core particles with the surfactant-based mesoporous shell comprises providing the TEOS and the BTESPD simultaneously.

13. The method of claim 1, wherein providing the TEOS and the BTESPD comprises providing within a range of about 1% TEOS to about 99% BTESPD to about 80% TEOS to about 20% BTESPD.

14. The method of claim 1, wherein coating the plurality of silica core particles with the surfactant-based mesoporous shell comprises selecting a ratio of the TEOS to the BTESPD for tuning a thickness of the surfactant-based mesoporous shell.

15. The method of claim 1, wherein etching the plurality of mesoporous coated silica core particles with the aqueous solution comprises stirring during the entire etching process at a rate of about 400 revolutions per minute (RPM) to about 1600 revolutions per minute (RPM).

16. The method of claim 1, wherein diffusing the payload into the plurality of hollow mesoporous particles results in a plurality of payload filled hollow mesoporous particles and a plurality of non-payload filled hollow mesoporous particles, wherein about 90% or greater of the plurality of hollow mesoporous particles are payload filled hollow mesoporous particles.

17. The method of claim 1, wherein the surfactant-based mesoporous shell comprises a thickness, wherein the thickness of the surfactant-based mesoporous shell determines a rate of release of the payload.

18. The method of claim 17, wherein the rate of release of the payload is slowed as a thickness of the surfactant-based mesoporous shell increases.

19. The method of claim 1, wherein the plurality of silica core particles are synthesized by:
   adding about 100 milliliters of 100% ethanol into about 2.8 milliliters of deionized water creating an ethanol-water solution in a first container;
   adding about 3.6 milliliters of ammonium hydroxide to the ethanol-water solution;
   stirring at a rate of about 400 revolutions per minute (RPM) at a temperature range of about 16 degrees Celsius to about 24 Celsius for about ten minutes;
   adding about 3.5 milliliters of the tetraethyl orthosilicate (TEOS) and sealing the first container; and
   stirring a resulting solution at about 400 revolutions per minute (RPM) for about twenty-four hours.

20. The method of claim 19, wherein coating the plurality of silica core particles with the surfactant-based mesoporous shell comprises:
   adding about 2.727 milliliters of 100% ethanol, about 27 microliters triethylamine, about 70 milligrams cetyltrimethylammonium bromide, and about 20 milliliters of deionized water in a second container;
   stirring at a rate of about 600 revolutions per minute (RPM) at a temperate of about 80 degrees Celsius for about 30 minutes;
   adding about 10 milliliters of the plurality of silica core particles from the first container into the second container and stirring for about 15 minutes;
   increasing the stirring rate to about 1400 revolutions per minute (RPM) while simultaneously adding about 87.5 microliters of the TEOS and about 37.5 microliters of the BTESPD and stirring for another 3 hours.

21. The method of claim 20, wherein etching the plurality of mesoporous coated silica core particles comprises:
   dissolving about 1540 milligrams of sodium carbonate to about 10 milliliters of deionized water in a third container;
   stirring the resulting solution at a temperature of about 50 degrees Celsius at a rate of about 600 revolutions per minute (RPM) for about one hour;
   increase the stirring rate to about 1200 revolutions per minute (RPM);
   adding 10 milliliters of the plurality of mesoporous coated silica core particles from the second container into the third container; and
   stirring for a time range of about eight hours to about nine hours.

\* \* \* \* \*